United States Patent
Smedley et al.

(10) Patent No.: US 7,951,155 B2
(45) Date of Patent: *May 31, 2011

(54) COMBINED TREATMENT FOR CATARACT AND GLAUCOMA TREATMENT

(75) Inventors: Gregory T. Smedley, Irvine, CA (US); David Haffner, Mission Viejo, CA (US); Barbara Niksch, Laguna Niguel, CA (US); Hosheng Tu, Newport Coast, CA (US); Thomas W. Burns, Laguna Niguel, CA (US)

(73) Assignee: Glaukos Corporation, Laguna Hills, CA (US)

(*) Notice: Subject to any disclaimer, the term of this patent is extended or adjusted under 35 U.S.C. 154(b) by 33 days.

This patent is subject to a terminal disclaimer.

(21) Appl. No.: 11/653,815

(22) Filed: Jan. 16, 2007

(65) Prior Publication Data

US 2007/0118147 A1 May 24, 2007

Related U.S. Application Data

(63) Continuation of application No. 10/165,616, filed on Jun. 7, 2002, now Pat. No. 7,163,543.

(60) Provisional application No. 60/364,988, filed on Mar. 15, 2002.

(51) Int. Cl.
 *A61F 9/00* (2006.01)
(52) U.S. Cl. ....................................... 606/107
(58) Field of Classification Search ............... 623/6.11, 623/6.12; 606/107, 108, 166, 4, 5, 6; 604/8
See application file for complete search history.

(56) References Cited

U.S. PATENT DOCUMENTS

| | | | |
|---|---|---|---|
| 3,788,327 A | 1/1974 | Donowitz et al. | |
| 4,037,604 A | 7/1977 | Newkirk | |
| 4,113,088 A | 9/1978 | Binkhorst | |
| 4,168,697 A | 9/1979 | Cantekin | |
| 4,175,563 A | 11/1979 | Arenberg et al. | |
| 4,366,582 A | 1/1983 | Faulkner | |
| 4,402,681 A * | 9/1983 | Haas et al. | 604/9 |
| 4,428,746 A * | 1/1984 | Mendez | 604/8 |
| 4,501,274 A | 2/1985 | Skjaerpe | |

(Continued)

FOREIGN PATENT DOCUMENTS

AU  200072059 A1  7/2001

(Continued)

OTHER PUBLICATIONS

Frank W. Newell, Ophthalmology Principles and Concepts, 1996, Anne S. Patterson/Mosby, Eighth edition, pp. 10-21 and 32.*

(Continued)

*Primary Examiner* — (Jackie) Tan-Uyen T Ho
*Assistant Examiner* — David Eastwood
(74) *Attorney, Agent, or Firm* — Knobbe Martens Olson & Bear LLP

(57) ABSTRACT

A method is provided for treatment of cataract in combination with a glaucoma procedure while maintaining the intraocular pressure by permitting aqueous to flow out of an anterior chamber of the eye through a surgically stented pathway. A trabecular stent is adapted for implantation within the trabecular meshwork of an eye such that intraocular liquid flows controllably from the anterior chamber of the eye to Schlemm's canal, bypassing the trabecular meshwork. Depending upon the specific treatment contemplated, pharmaceuticals may be utilized in conjunction with the trabecular stent enabling post-cataract healing processes.

23 Claims, 16 Drawing Sheets

U.S. PATENT DOCUMENTS

| | | | |
|---|---|---|---|
| 4,521,210 | A | 6/1985 | Wong |
| 4,554,918 | A | 11/1985 | White |
| 4,560,383 | A | 12/1985 | Leiske |
| 4,583,224 | A | 4/1986 | Ishii et al. |
| 4,604,087 | A | 8/1986 | Joseph |
| 4,632,842 | A | 12/1986 | Karwoski et al. |
| 4,634,418 | A | 1/1987 | Binder |
| 4,718,907 | A | 1/1988 | Karwoski et al. |
| 4,722,724 | A | 2/1988 | Schocket |
| 4,733,665 | A | 3/1988 | Palmaz |
| 4,750,901 | A | 6/1988 | Moltena |
| 4,787,885 | A | 11/1988 | Binder |
| 4,804,382 | A | 2/1989 | Turina et al. |
| 4,820,626 | A | 4/1989 | Williams et al. |
| 4,846,172 | A | 7/1989 | Berlin |
| 4,846,793 | A | 7/1989 | Leonard et al. |
| 4,853,224 | A | 8/1989 | Wong |
| 4,863,457 | A | 9/1989 | Lee |
| 4,883,864 | A | 11/1989 | Scholz |
| 4,886,488 | A | 12/1989 | White |
| 4,900,300 | A | 2/1990 | Lee |
| 4,936,825 | A | 6/1990 | Ungerleider |
| 4,946,436 | A | 8/1990 | Smith |
| 4,968,296 | A | 11/1990 | Ritch et al. |
| 4,997,652 | A | 3/1991 | Wong |
| 5,005,577 | A | 4/1991 | Frenkel |
| 5,041,081 | A | 8/1991 | Odrich |
| 5,073,163 | A | 12/1991 | Lippman |
| 5,092,837 | A | 3/1992 | Ritch et al. |
| 5,095,887 | A | 3/1992 | Leon et al. |
| 5,127,901 | A | 7/1992 | Odrich |
| 5,129,895 | A | 7/1992 | Vassiliadis et al. |
| 5,164,188 | A | 11/1992 | Wong |
| 5,171,213 | A | 12/1992 | Price, Jr. |
| 5,178,604 | A | 1/1993 | Baerveldt et al. |
| 5,180,362 | A | 1/1993 | Worst |
| 5,207,685 | A | 5/1993 | Cinberg et al. |
| 5,246,451 | A | 9/1993 | Trescony et al. |
| 5,290,295 | A | 3/1994 | Querals et al. |
| 5,300,020 | A | 4/1994 | L'Esperance, Jr. |
| 5,318,513 | A | 6/1994 | Leib et al. |
| 5,334,137 | A | 8/1994 | Freeman |
| 5,338,291 | A | 8/1994 | Speckman et al. |
| 5,346,464 | A | 9/1994 | Camras |
| 5,360,399 | A | 11/1994 | Stegmann |
| 5,370,607 | A | 12/1994 | Memmen |
| 5,370,641 | A | 12/1994 | O'Donnell, Jr. |
| 5,372,577 | A | 12/1994 | Ungerleider |
| 5,397,300 | A | 3/1995 | Baerveldt et al. |
| 5,433,701 | A | 7/1995 | Rubinstein |
| 5,443,505 | A | 8/1995 | Wong et al. |
| 5,454,796 | A | 10/1995 | Krupin |
| 5,472,440 | A | 12/1995 | Beckman |
| 5,476,445 | A | 12/1995 | Baerveldt et al. |
| 5,486,165 | A | 1/1996 | Stegmann |
| 5,502,052 | A | 3/1996 | DeSantis |
| 5,516,522 | A | 5/1996 | Peyman et al. |
| 5,520,631 | A | 5/1996 | Nordquist et al. |
| 5,547,993 | A | 8/1996 | Miki |
| 5,557,453 | A | 9/1996 | Schalz et al. |
| 5,558,629 | A | 9/1996 | Baerveldt et al. |
| 5,558,630 | A | 9/1996 | Fisher |
| 5,558,637 | A | 9/1996 | Allonen et al. |
| 5,562,641 | A | 10/1996 | Flomenblit et al. |
| RE35,390 | E | 12/1996 | Smith |
| 5,601,094 | A | 2/1997 | Reiss |
| 5,601,549 | A | 2/1997 | Miyagi |
| 5,626,558 | A | 5/1997 | Suson |
| 5,626,559 | A | 5/1997 | Solomon |
| 5,639,278 | A | 6/1997 | Dereume et al. |
| 5,651,783 | A | 7/1997 | Reynard |
| 5,652,236 | A | 7/1997 | Krauss |
| 5,663,205 | A | 9/1997 | Ogawa et al. |
| 5,665,114 | A | 9/1997 | Weadock et al. |
| 5,670,161 | A | 9/1997 | Healy et al. |
| 5,676,679 | A | 10/1997 | Simon et al. |
| 5,681,275 | A | 10/1997 | Ahmed |
| 5,681,323 | A | 10/1997 | Arick |
| 5,702,414 | A | 12/1997 | Richter et al. |
| 5,702,419 | A | 12/1997 | Berry et al. |
| 5,704,907 | A | 1/1998 | Nordquist et al. |
| 5,713,844 | A | 2/1998 | Peyman |
| 5,723,005 | A | 3/1998 | Herrick |
| 5,733,256 | A * | 3/1998 | Costin ............................ 604/22 |
| 5,741,333 | A | 4/1998 | Frid |
| 5,743,868 | A | 4/1998 | Brown et al. |
| 5,752,928 | A | 5/1998 | de Roulhac et al. |
| 5,766,242 | A | 6/1998 | Wong et al. |
| 5,766,243 | A | 6/1998 | Christensen et al. |
| 5,767,079 | A | 6/1998 | Glaser et al. |
| 5,785,674 | A | 7/1998 | Mateen |
| 5,807,302 | A | 9/1998 | Wandel |
| 5,810,870 | A | 9/1998 | Myers et al. |
| 5,814,620 | A | 9/1998 | Robinson et al. |
| 5,824,072 | A | 10/1998 | Wong |
| 5,830,139 | A | 11/1998 | Abrue |
| 5,830,171 | A | 11/1998 | Wallace |
| 5,833,694 | A | 11/1998 | Poncet |
| 5,836,939 | A | 11/1998 | Negus et al. |
| 5,840,041 | A | 11/1998 | Petter et al. |
| 5,865,831 | A * | 2/1999 | Cozean et al. ............... 606/6 |
| 5,868,697 | A | 2/1999 | Ritcher et al. |
| 5,869,468 | A | 2/1999 | Freeman |
| 5,879,319 | A | 3/1999 | Pynson et al. |
| 5,882,327 | A | 3/1999 | Jacob |
| 5,886,822 | A | 3/1999 | Spitzer |
| 5,893,837 | A | 4/1999 | Eagles et al. |
| 5,908,449 | A | 6/1999 | Bruchman et al. |
| 5,925,342 | A | 7/1999 | Adorante et al. |
| 5,932,299 | A | 8/1999 | Katoot |
| 5,952,378 | A | 9/1999 | Stjernschantz et al. |
| 5,968,058 | A * | 10/1999 | Richter et al. ............... 606/166 |
| 5,980,928 | A | 11/1999 | Terry |
| 5,981,598 | A | 11/1999 | Tatton |
| 6,004,302 | A | 12/1999 | Brierley |
| 6,007,510 | A | 12/1999 | Nigam |
| 6,007,511 | A | 12/1999 | Prywes |
| 6,033,434 | A | 3/2000 | Borghi |
| 6,045,557 | A | 4/2000 | White et al. |
| 6,050,970 | A | 4/2000 | Baeveldt |
| 6,050,999 | A | 4/2000 | Paraschac et al. |
| 6,059,772 | A | 5/2000 | Hsia et al. |
| 6,059,812 | A | 5/2000 | Clerc et al. |
| 6,060,463 | A | 5/2000 | Freeman |
| 6,063,116 | A | 5/2000 | Kelleher |
| 6,063,396 | A * | 5/2000 | Kelleher ...................... 424/428 |
| 6,071,286 | A | 6/2000 | Mawad |
| 6,077,299 | A | 6/2000 | Adelberg et al. |
| 6,102,045 | A | 8/2000 | Nordquist et al. |
| 6,110,912 | A | 8/2000 | Kaufman et al. |
| 6,123,668 | A | 9/2000 | Abreu |
| 6,142,990 | A | 11/2000 | Burk |
| 6,159,458 | A | 12/2000 | Bowman et al. |
| 6,165,210 | A | 12/2000 | Lau et al. |
| 6,168,575 | B1 | 1/2001 | Soltanpour |
| 6,174,305 | B1 | 1/2001 | Mikus et al. |
| 6,177,427 | B1 | 1/2001 | Clark et al. |
| 6,184,250 | B1 | 2/2001 | Klimko et al. |
| 6,186,974 | B1 | 2/2001 | Allan et al. |
| 6,187,016 | B1 | 2/2001 | Hedges et al. |
| 6,193,656 | B1 | 2/2001 | Jeffries et al. |
| 6,194,415 | B1 | 2/2001 | Wheeler et al. |
| 6,197,056 | B1 | 3/2001 | Schachar |
| 6,201,001 | B1 | 3/2001 | Wang et al. |
| 6,203,513 | B1 | 3/2001 | Yaron et al. |
| 6,217,895 | B1 | 4/2001 | Guo et al. |
| 6,228,873 | B1 | 5/2001 | Brandt et al. |
| 6,231,597 | B1 * | 5/2001 | Deem et al. ............... 623/1.12 |
| 6,231,853 | B1 | 5/2001 | Hillman et al. |
| 6,241,721 | B1 * | 6/2001 | Cozean et al. ............... 606/6 |
| 6,251,090 | B1 | 6/2001 | Avery et al. |
| 6,254,612 | B1 | 7/2001 | Hieshima |
| 6,261,256 | B1 | 7/2001 | Ahmed |
| 6,266,182 | B1 | 7/2001 | Morita |
| 6,268,398 | B1 | 7/2001 | Ghosh et al. |
| 6,274,138 | B1 | 8/2001 | Bandman et al. |
| 6,287,256 | B1 | 9/2001 | Park et al. |

| | | |
|---|---|---|
| 6,287,313 B1 | 9/2001 | Sasso |
| 6,299,895 B1 | 10/2001 | Hammang et al. |
| 6,331,313 B1 | 12/2001 | Wong et al. |
| 6,342,058 B1 | 1/2002 | Portney |
| 6,348,042 B1 | 2/2002 | Warren, Jr. |
| 6,375,642 B1 | 4/2002 | Grieshaber et al. |
| 6,413,540 B1 | 7/2002 | Yaacobi |
| 6,416,777 B1 | 7/2002 | Yaacobi |
| 6,428,501 B1 | 8/2002 | Reynard |
| 6,436,427 B1 | 8/2002 | Hammang et al. |
| 6,450,937 B1 | 9/2002 | Mercereau et al. |
| 6,450,984 B1 | 9/2002 | Lynch et al. |
| 6,464,724 B1 | 10/2002 | Lynch et al. |
| 6,494,857 B1 | 12/2002 | Neuhann |
| 6,524,275 B1 | 2/2003 | Lynch et al. |
| 6,530,896 B1 | 3/2003 | Elliott |
| 6,533,768 B1 | 3/2003 | Hill |
| 6,544,249 B1 | 4/2003 | Yu et al. |
| 6,548,078 B2 | 4/2003 | Guo et al. |
| 6,579,235 B1 | 6/2003 | Abita et al. |
| 6,585,680 B2 | 7/2003 | Bugge |
| 6,595,945 B2 | 7/2003 | Brown |
| 6,622,473 B2 | 9/2003 | Lynch et al. |
| 6,626,858 B2 | 9/2003 | Lynch et al. |
| 6,629,981 B2 | 10/2003 | Bui et al. |
| 6,638,239 B1 | 10/2003 | Bergheim et al. |
| 6,666,841 B2 | 12/2003 | Gharib et al. |
| 6,699,211 B2 | 3/2004 | Savage |
| D490,152 S | 5/2004 | Myall et al. |
| 6,736,791 B1 | 5/2004 | Tu et al. |
| 6,780,165 B2 | 8/2004 | Kadziauskas et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,955,656 B2 | 10/2005 | Bergheim et al. |
| 7,033,603 B2 | 4/2006 | Nelson et al. |
| 7,041,077 B2 | 5/2006 | Shields |
| 7,094,225 B2 | 8/2006 | Tu et al. |
| 7,135,009 B2 | 11/2006 | Tu et al. |
| 7,291,125 B2 | 11/2007 | Coroneo |
| 7,662,123 B2 | 2/2010 | Shields |
| 2002/0013546 A1 | 1/2002 | Grieshaber et al. |
| 2002/0013572 A1* | 1/2002 | Berlin ............................ 606/4 |
| 2002/0026200 A1 | 2/2002 | Savage |
| 2002/0072673 A1 | 6/2002 | Yamamoto et al. |
| 2002/0099434 A1 | 7/2002 | Buscemi et al. |
| 2002/0133168 A1 | 9/2002 | Smedley et al. |
| 2002/0143284 A1 | 10/2002 | Tu et al. |
| 2002/0188308 A1* | 12/2002 | Tu et al. .................... 606/167 |
| 2003/0055372 A1 | 3/2003 | Lynch et al. |
| 2003/0060752 A1 | 3/2003 | Bergheim et al. |
| 2003/0069637 A1 | 4/2003 | Lynch et al. |
| 2003/0088260 A1 | 5/2003 | Smedley et al. |
| 2003/0097151 A1 | 5/2003 | Smedley et al. |
| 2003/0181848 A1 | 9/2003 | Bergheim et al. |
| 2003/0187384 A1 | 10/2003 | Bergheim et al. |
| 2003/0187385 A1 | 10/2003 | Bergheim et al. |
| 2003/0229303 A1 | 12/2003 | Haffner et al. |
| 2003/0236483 A1 | 12/2003 | Ren |
| 2003/0236484 A1 | 12/2003 | Lynch et al. |
| 2004/0024345 A1 | 2/2004 | Gharib et al. |
| 2004/0050392 A1 | 3/2004 | Tu et al. |
| 2004/0102729 A1 | 5/2004 | Haffner et al. |
| 2004/0111050 A1 | 6/2004 | Smedley et al. |
| 2004/0127843 A1 | 7/2004 | Tu et al. |
| 2004/0225250 A1 | 11/2004 | Yablonski |
| 2004/0254520 A1 | 12/2004 | Porteous et al. |
| 2004/0254521 A1 | 12/2004 | Simon |
| 2005/0038334 A1 | 2/2005 | Lynch et al. |
| 2005/0049578 A1 | 3/2005 | Tu et al. |
| 2005/0107734 A1 | 5/2005 | Coroneo |
| 2005/0119737 A1 | 6/2005 | Bene et al. |
| 2005/0192527 A1 | 9/2005 | Gharib et al. |
| 2006/0069340 A1 | 3/2006 | Simon |
| 2007/0191863 A1 | 8/2007 | De Juan, Jr. et al. |
| 2007/0202186 A1 | 8/2007 | Yamamoto et al. |
| 2007/0233037 A1 | 10/2007 | Gifford, III et al. |
| 2008/0027304 A1 | 1/2008 | Pardo et al. |
| 2008/0058704 A1 | 3/2008 | Hee et al. |
| 2008/0306429 A1 | 12/2008 | Shields et al. |
| 2009/0043321 A1 | 2/2009 | Conston et al. |
| 2010/0173866 A1 | 7/2010 | Hee et al. |

FOREIGN PATENT DOCUMENTS

| | | |
|---|---|---|
| CA | 2244646 A1 | 2/1999 |
| DE | 198 40 047 A1 | 3/2000 |
| EP | 0 858 788 A1 | 8/1998 |
| EP | 0 898 947 A2 | 3/1999 |
| EP | 1 114 627 A1 | 7/2001 |
| FR | 2 710 269 A1 | 3/1995 |
| FR | 2 721 499 | 12/1995 |
| GB | 2 296 663 A | 7/1996 |
| JP | 11-123205 | 5/1999 |
| RU | 2143250 C1 | 12/1999 |
| WO | WO 89/00869 A1 | 2/1989 |
| WO | WO 91/18568 A1 | 12/1991 |
| WO | WO 92/19294 | 11/1992 |
| WO | WO/94/13234 | 6/1994 |
| WO | WO 94/21205 A1 | 9/1994 |
| WO | WO 95/08310 A1 | 3/1995 |
| WO | WO 96/20742 A1 | 7/1996 |
| WO | WO 98/30181 A1 | 7/1998 |
| WO | WO 98/35639 A1 | 8/1998 |
| WO | WO 99/26567 A1 | 6/1999 |
| WO | WO 99/30641 A1 | 6/1999 |
| WO | WO 99/38470 A2 | 8/1999 |
| WO | WO 99/38470 A3 | 8/1999 |
| WO | WO 00/13627 A1 | 3/2000 |
| WO | WO 00/64389 A1 | 11/2000 |
| WO | WO 00/64390 A1 | 11/2000 |
| WO | WO 00/64391 A1 | 11/2000 |
| WO | WO 00/64393 A1 | 11/2000 |
| WO | WO 00/72788 A1 | 12/2000 |
| WO | WO 01/50943 A2 | 7/2001 |
| WO | WO 01/78631 A2 | 10/2001 |
| WO | WO 01/78656 A2 | 10/2001 |
| WO | WO 03/015659 A2 | 2/2003 |
| WO | WO 03/073968 A2 | 9/2003 |

OTHER PUBLICATIONS

Phillip C. Jacobi, MD, Thomas S. Dietlein, MD and Gunter K. Krieglstein, MD, Goniocurettage for Removing Trabecular Meshwork: Clinical Results of a new Surgical Technique in Advanced Chronic Open-Angle Glaucoma, *American Journal of Ophthalmology*, May 1999, pp. 505-510.

Phillip C. Jacobi, MD, Thomas S. Dietlein, MD and Gunter K. Krieglstein, MD, Bimanual Trabecular Aspiration in Pseudoexfoliation Glaucoma, *Ophthalmology*. 1998, vol. 105, No. 5, May 1998, pp. 886-894.

Phillip C. Jacobi, MD, Thomas S. Dietlein, MD and Gunter K. Krieglstein, MD, Microendoscopic Trabecular Surgery in Glaucoma Management, *Ophthalmology*, 1999 vol. 106, No. 3, pp. 538-544.

Arthur L. Schwartz, MD, & Douglas R. Anderson, MD, Trabecular Surgery, *Arch Ophthalmol*, vol. 92, Aug. 1974, pp. 134-138.

R.A. Hill, Q. Ren, D.C. Nguyen, L.H. Liaw, & M.W. Berns, Free-election Laser (FEL) Ablation of Ocular Tissues, *Laser Med Sci* 1998, vol. 13, pp. 219-226.

Maurice H. Luntz, MD & D.G. Livingston, B.SC., Trabeculotomy AB Externo & Trabeculectomy in Congenital and Adult-Onset Glaucoma, *American Journal of Ophthalmology*, Feb. 1977, vol. 83, No. 2, pp. 174-179.

W.M. Grant, MD, Further Studies on Facility of Flow Through the Trabecular Meshwork, *AMA Archives of Ophthalmology*, Oct. 1958, vol. 60, pp. 523-533.

Richard A. Hill, MD, George Baerveldt, MD, Serdar A. Ozler, MD, Michael Pickford, BA, Glen A. Profeta, BS, & Michael W. Berns, PhD, Laser Trabecular Ablation (LTA), *Laser in Surgery and Medicine*, 1991, vol. 11, pp. 341-346.

Detliev Spiegel, MD, Karin Kobuch, MD, Richard A. Hill, MD, Ronald L. Gross, MD, Schlemm's Canal Implant: A New Method to Lower Intraocular Pressure in Patients With POAG, *Opthalmic Surgery and Lasers*, Jun. 1999, vol. 30, No. 6, pp. 492-494.

L. Jay Katz, MD, A Call for Innovative Operations for Glaucoma, *Arch Ophthalmology*, Mar. 2000, vol. 118, pp. 412-413.

Anselm Kampik & Franz Grehn, Nutzen und Risiken Augenärzticher Therapie, *Hauptreferate der XXXIII, Essener Fortbildung für Augenärzte*, Dec. 1998. (English translated version enclosed Benefits and Risks of Ophthalmological Therapy).

Detlev Spiegel, *7 chirurgische Glaukomtherapie*, pp. 79-88 (English translation enclosed).

U.S. Appl. No. 09/452,963, filed Dec. 2, 1999, entitled: *Expandable/Retractable Stent For Venous And Valvular Annulus Use*.

Hans Hoerauf, Christopher Wirbelauer, Christian Scholz, Ralf Engelhardt, Peter Koch, Horst Laqua, and Reginald Birngruber, *Slit-Lamp-Adapted Optical Coherence Tomography of the Anteriuor Segment*, Graefe's Arch Clin. Exp. Ophthalmol, May 1999, vol. 238, pp. 8-18.

Sumita Radhakrishnan, Andrew M. Rollins, Jonathan E. Roth, S. Yazddanfar, Volker Westphal, David Bardenstein, and Joseph Izatt, *Real-Time Optical Coherence Tomography of the Anterior Segment at 1310 nm*, Arch Ophthalmology, Aug. 2001, vol. 119, pp. 1179-1185.

I. Grierson, R.C. Howes, and Q. Wang, *Age-related Changes in the Canal of Schlemm*, Exp. Eye Res., 1984, vol. 39, pp. 505-512.

Luanna K. Putney, Cecile Rose T. Vibat, and Martha E. O'Donnell, *Intracellular Cl Regulates Na-K-Cl Cotransport Activity in Human Trabecular Meshwork Cells*, 1999 American Physiological Society, Sep. 1999, pp. C373 through C383.

Edited by Kevin Strange, *Cellular and Molecular Physiology of Cell Volume Regulation*, Library of Congress Cataloging in-Publication Data, CRC Press, Inc., pp. 312-321.

William Tatton, Ruth M.E. Chalmers-Redman, Ajay Sud, Steven M. Podos, and Thomas Mittag, *Maintaining Mitochondrial Membrane Impermeability: An Opportunity for New Therapy in Glaucoma*, Survey of Ophthalmology, vol. 45, Supplement 3, May 2001, pp. S277 through S283.

Robert W. Nickells, *Apoptosis of Retinal Ganglion Cells in Glaucoma: An Update of the Molecular Pathways Involved in Cell Death*, Survey of Ophthalmology, vol. 43, Supplement 1, Jun. 1999, pp. S-151 through S161.

Grune & Stratton, Harcourt Brace Jovanovich Publishers, edited by J.E. Cairns, *Glaucoma*, vol. 1, Chapter 14, *Anatomy of the Aqueous Outflow Channels*, by Johannes W. Rohen, pp. 277-296.

Yasuhiro Matsumoto and Douglas H. Johnson, *Trabecular Meshwork Phagocytosis in Graucomatous Eyes*, Ophthalmologica 1977, vol. 211, pp. 147-152.

M. Bruce Shields, MD, *A Study Guide for Glaucoma: Aqueous Humor Dynamics*, Copyright 1982, pp. 6-43.

M.A. Johnstone, R. Stegmann, and B.A. Smit, *American Glaucoma Society, 12th Annual Meeting, Cylindrical Tubular Structures Spanning from Trabecular Meshwork Across SC*, Laboratory Studies with SEM, TEM and Tracers Correlated with Clinical Findings, p. 39.

W.G. Tatton, *Apoptotic Mechanisms in Neurodegeneration: Possible Relevance to Glaucoma*, European Journal of Ophthalmology, Jan.-Mar. 1999, vol. 9, Supplement 1, pp. S22 through S29.

Cindy K. Bahler, BS, Gegrory T. Smedley, PhD, Jianbo Zhou, PhD, Douglas H. Johnson, MD., *American Journal of Ophthalmology*, Dec. 2004, vol. 138.

Jianbo Zhou, PhD, Gregory T. Smedley, PhD., *A Trabecular Bypass Flow Hypothesis*, Feb. 2005, vol. 14 No. 1.

U.S. Appl. No. 09/452,963, filed Dec. 2, 1999. Title: *Expandable/Retractable Stent for Venous and Valvular Annulus Use*.

Vincente, L. Jocson, M.D.; *Air Trabeculotomy*; American Journal of Ophthalmolgy: vol. 79, No. 1, Jan.-Jun. 1975; pp. 107-111.

Daniel A. Fletcher, Ph.D., Daniel V. Palanker, Ph.D., Philip Hule, M.D., Jason Miller, MS, Michael F. Marmor, M.D. and Mark S. Blumenkranz, M.D.; *Intravascular Drug Delivery With a Pulsed Liquid Microjet*; (Reprinted) Arch Ophthalmology; vol. 120, Sep. 2002, pp. 1206-1208.

Troncoso, Manuel U., Tantalum implants for inducing hypotony, American Journal of Ophthalmology, vol. 32, No. 4, Apr. 1949, pp. 499-508 (11 pages).

Jens F. Jordan, Thomas S. Dietlein, Sven Dinslage, Christoph Lüke, Walter Konen, Günter K. Krieglstein, *Cyclodialysis ab interno as a surgical approach to intractable glaucoma*, Graefe's Arch Clin Exp Ophthalmol (2007) 245:1071-1076.

Jens F. Jordan, MD; Bert F. Engels, MD; Sven Dinslage, MD; Thomas S. Dietlein, MD; Helen D. Ayertey, MD; Sigrid Roters, MD; Peter Esser, MD; Walter Konen, MD; and Günter K. Krieglstein, MD, *A Novel Approach to Suprachoroidal Drainage for the Surgical Treatment of Intractable Glaucoma*, J Glaucoma, vol. 15, No. 3, Jun. 2006, pp. 200-205.

M. Klemm, A. Balazs, J. Draeger, R. Wiezorrek, *Experimental use of space-retaining substances with extended duration: functional and morphological results*, Graefe's Arch Clin Exp Opbhthalmol (1995) 233:592-597.

Timothy W. Olson, MD; Xiao Feng, MD; Kathy Wabner, BA; Stanley R. Conston, BS; David H. Sierra, Ph.D.; David V. Folden, MD; Morton E. Smith, MD; and J. Douglas Cameron, MD, *Cannulation of the Suprachoroidal Space: A Novel Drug Delivery Methodology to the Posterior Segment*, American Journal of Ophthalmology, vol. 142, No. 5, Nov. 2006, pp. 777-787.e2.

Rosenberg, et al., "Implants in Glaucoma Surgery", The Glaucomas, 1996, Chapter 88, pp. 1783-1807 (27 pages).

Patrick J. Rowan, MD, *Combined Cyclodialysis and Cataract Surgery*, Ophthalmic Surgery and Lasers, Dec. 1998, vol. 29, No. 12, pp. 962-968 (9 pages).

Manuel Uribe Troncoso, M.D., *Cyclodialysis with Insertion of a Metal Implant in the Treatment of Glaucoma*, Read before the Section on Ophthalmology at the Ninetieth Annual Session of the American Medical Association, St. Louis, May 17, 1939, Archives of Ophthalmology, pp. 270-300, downloaded from www.archophthalmol.com on Aug. 5, 2010.

Wagner, Justin A., Edwards, Aurélie, and Schuman, Joel S., *Characterization of Uveoscleral Outflow in Enucleated Porcine Eyes Perfused Under Constant Pressure*, Invest Ophthalmol Vis Sci. Sep. 2004; 45(9): 3203-3206 (9 pages).

\* cited by examiner

COMBINED TREATMENT FOR CATARACT AND GLAUCOMA TREATMENT

CROSS REFERENCE TO RELATED APPLICATIONS

This application is a continuation of U.S. patent application Ser. No. 10/165,616, filed Jun. 7, 2002, now U.S. Pat. No. 7,163,543, issued Jan. 16, 2007, entitled "Combined Treatment for Cataract and Glaucoma Treatment," which claims the benefit of U.S. Provisional Patent Application Ser. No. 60/364,988, filed Mar. 15, 2002, entitled "Methods for Treating Combined Glaucoma and Cataract," the entire contents of each on of which are hereby incorporated by reference herein.

BACKGROUND OF THE INVENTION

1. Field of the Invention

The invention relates generally to surgical procedures for treating cataract. More particularly, it relates to a treatment of cataract in combination with an ab interno procedure for maintaining the intraocular pressure by permitting intraocular liquid to flow out of an anterior chamber of the eye through a surgically stented pathway.

2. Description of the Related Art

As is well known in the art, a human eye is a specialized sensory organ capable of light reception and is able to receive visual images. Aqueous humor is a transparent liquid that fills the region between the cornea, at the front of the eye, and the lens. A trabecular meshwork, located in an anterior chamber angle formed between the iris and the cornea, serves as a drainage channel for intraocular liquid from the anterior chamber, which maintains a balanced pressure within the anterior chamber of the eye.

Artificial intraocular lenses are widely used to replace the human crystalline lens of the eye. The human crystalline lens is a living transparent structure composed primarily of protein having a thickness of about five millimeters and a diameter of about nine millimeters. The lens is suspended behind the iris by zonula fibers that connect the lens to the ciliary body. A lens capsule surrounds the lens; the front portion of the capsule is generally referred to as the anterior capsule and the back portion is generally referred to as the posterior capsule.

The term "cataract" refers to the opacity of the lens of the eye. There are a variety of types of cataracts and for most cataracts, surgical intervention is required to remove and replace the lens with an artificial intraocular lens.

There are a number of procedures and devices that have been developed for the removal of the natural lens followed by the insertion of an artificial lens. The extraction procedure can generally be categorized as intracapsular (i.e., where the lens is removed together with the lens capsule) or extracapsular (such as where a portion of the anterior capsule is circularly removed (capsulorhexis) and the posterior capsule is left intact).

Presently, phacoemulsification is a widely used method for the removal of diseased or damaged natural lens tissue. The phacoemulsification process generally employs a small incision typically of about 2 millimeters (mm) to about 4 mm in length through the cornea and a probe is used to ultrasonically break apart and remove the crystalline lens through the capsulorhexis.

SUMMARY OF THE INVENTION

During the cataract surgical procedure and immediately after the procedure, it is important to maintain the intraocular pressure at a desired level. This is particularly important to a subset of cataract patients that also has glaucoma. Therefore, there remains a clinical need for maintaining the intraocular pressure for cataract surgical treatment by allowing drainage of intraocular liquid or fluid through a hollow stented pathway bypassing the trabecular meshwork. The term "intraocular liquid (or fluid)" is herein intended to mean the aqueous humor, the viscoelastic fluid, the normal physiological saline or the like that stays in the eye at one time or the other.

Historically, about two percent of people in the United States have glaucoma. Glaucoma is a separate disease from cataract; however, some patients have both glaucoma and cataract so that is reasonable to treat both in a combined procedure. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor (herein also referred to as "aqueous" and is one component of the "intraocular liquid (or fluid)" referred to herein) to enter Schlemm's canal, which then empties into aqueous collector channels in the posterior wall of Schlemm's canal and then into aqueous veins, which form the episcleral venous system.

Aqueous is continuously secreted by a ciliary body around the lens, so there is a constant flow of aqueous from the ciliary body to the anterior chamber of the eye. Pressure within the eye is determined by a balance between the production of aqueous and its exit through the trabecular meshwork (major route) and uveal scleral outflow (minor route). The portion of the trabecular meshwork adjacent to Schlemm's canal (the juxtacanilicular meshwork) causes most of the resistance to aqueous outflow.

Because the trabecular meshwork and juxtacanilicular tissue together provide the majority of resistance to the outflow of aqueous, they are logical targets for surgical channeling with a stented pathway during and after cataract surgery for maintaining balanced intraocular pressure. Various embodiments of glaucoma shunts are disclosed herein for aqueous to exit through the trabecular meshwork (major route) or uveal scleral outflow (minor route) or other route effective to reduce intraocular pressure (IOP). In some glaucoma patients, this surgical channeling may become the only viable alternative for lowering the intraocular pressure because of the patient's intolerance to glaucoma medicine immediately after cataract surgery.

What is desirable, therefore, is a combined procedure of ab interno trabecular stenting followed by a cataract treatment. The stenting advantageously provides for aqueous drainage to maintain substantially balanced intraocular pressure during and after the procedure. Moreover, and advantageously, the combined procedure is fast, safe, and less expensive than currently available two-procedure modalities.

Advantageously, the accompanying glaucoma (or lowering IOP) procedure provides the eye with a balanced intraocular pressure post-operatively without the need of an IOP-lowering drug that may complicate the surgical success of the intended cataract procedure. Another advantage is that, a single incision in the cornea or sclera may be used to perform both surgical procedures. Moreover, and desirably, the glaucoma (or elevated IOP) and cataract may be treated in a single visit operation that may be performed as an outpatient procedure with rapid visual recovery and greatly decreased morbidity.

In accordance with one embodiment, a method is provided for treating cataract of an eye while maintaining normal physiological intraocular pressure. The method comprising combination steps of establishing an opening through trabecular meshwork (also referred herein as "trabecular opening") for maintaining normal physiological intraocular pressure, removing the cataract, and inserting an intraocular lens.

One aspect of the invention provides a trabecular stent having a lumen therein for inserting within the opening through trabecular meshwork. The step of establishing the opening through trabecular meshwork is by an ab interno procedure, wherein the ab interno procedure comprises delivering the trabecular stent through an incision on a cornea of the eye remote from the trabecular opening. The incision may be self-sealing.

The trabecular stent is adapted for implantation within a trabecular meshwork of an eye such that intraocular liquid flows controllably from an anterior chamber of the eye to Schlemm's canal. The trabecular stent may comprise a quantity of pharmaceuticals effective in treating glaucoma and/or cataract, which are controllably released from the device into cells of the trabecular meshwork and/or Schlemm's canal. Depending upon the specific treatment contemplated, pharmaceuticals may be utilized in conjunction with the trabecular stent such that liquid or aqueous flow either increases or decreases as desired. Placement of the trabecular stent within the eye and incorporation, and eventual release, of a proven pharmaceutical glaucoma therapy will reduce, inhibit or slow the effects of glaucoma and/or heal the injury from cataract procedure.

Another aspect of the invention provides a method of treating glaucoma or eye diseases around trabecular meshwork. The method comprises providing at least one pharmaceutical substance incorporated into a trabecular stent, implanting the trabecular stent within a trabecular meshwork of an eye such that a first end of the trabecular stent is positioned in an anterior chamber of the eye while a second end is positioned in a Schlemm's canal, and allowing the stent to release a quantity of the pharmaceutical substance into the eye or eye tissue. The first and second ends of the trabecular stent establish a fluid communication between the anterior chamber and Schlemm's canal to assist maintaining a normal physiological intraocular pressure during or after the cataract procedure. The normal physiological intraocular pressure is maintained between about 10 mmHg and 21 mmHg.

In another aspect of the invention, a method of regulating aqueous humor outflow within an eye is provided. The method comprises creating an incision in a trabecular meshwork of the eye, wherein the incision is substantially parallel with a circumference of a limbus of the eye, inserting an outlet section of a trabecular stent through the incision into Schlemm's canal such that the outlet section resides within Schlemm's canal while an inlet section of the trabecular stent resides in the anterior chamber, initiating an outflow of aqueous humor from the anterior chamber through the trabecular stent into Schlemm's canal, and continuously maintaining the outflow of aqueous humor during and after the cataract procedure so as to maintain a normal physiological intraocular pressure during or after the cataract procedure.

Still another aspect of the invention provides a method of regulating intraocular pressure within an eye. The method comprises making an incision passing into a trabecular meshwork of the eye, wherein the incision is oriented lengthwise substantially parallel with a circumference of a limbus. The incision establishes a fluid communication between an anterior chamber and Schlemm's canal of the eye. The method further comprises implanting a hollow trabecular stent through the incision such that an outlet section of the trabecular stent resides within Schlemm's canal and an inlet section of the trabecular stent resides within the anterior chamber. The method still further comprises establishing a fluid transfer from the anterior chamber through the trabecular stent into Schlemm's canal.

Another aspect of the invention provides a method of implanting a trabecular stent within an eye. The method known as an ab interno procedure herein comprises creating a first incision in a cornea on a first side of the eye, wherein the first incision passes through the cornea into an anterior chamber of the eye. The method further comprises passing (across or U-turnedly) an incising device through the first incision and moving a distal end of the incising device passing the anterior chamber to a trabecular meshwork residing on a second side of the eye, and using the incising device to create a second incision. The second incision is in the trabecular meshwork, passing from the anterior chamber through the trabecular meshwork into Schlemm's canal. In one alternate embodiment, the first incision in the cornea may be a very short distance from the second incision in the trabecular meshwork. The method further comprises inserting the trabecular stent into a distal space of a delivery applicator. The delivery applicator comprises a cannula portion having a distal end and a proximal end attached to a syringe portion. The cannula portion has at least one lumen and at least one irrigating hole disposed between proximal and distal ends of the cannula portion. The irrigating hole is in fluid communication with the lumen. The distal space comprises a holder that holds the trabecular stent device during delivery and releases the trabecular stent when a practitioner activates deployment mechanism of the stent device. The method further comprises advancing the cannula portion and the trabecular stent through the first incision, across or U-turnedly passing the anterior chamber and into the second incision, wherein an outlet section of the trabecular stent is implanted into Schlemm's canal while an inlet section of the trabecular stent remains in fluid communication with the anterior chamber. The method still further comprises releasing the trabecular stent from the holder of the delivery applicator.

In accordance with some embodiments, a method is provided for treatment of cataract in combination with a glaucoma procedure while maintaining the intraocular pressure by permitting aqueous to flow out of an anterior chamber of the eye through a surgically stented pathway. A trabecular stent is adapted for implantation within the trabecular meshwork of an eye such that intraocular liquid flows controllably from the anterior chamber of the eye to Schlemm's canal, bypassing the trabecular meshwork. Depending upon the specific treatment contemplated, pharmaceuticals may be utilized in conjunction with the trabecular stent enabling post-cataract healing processes.

In accordance with one embodiment, a method is provided of performing surgery to lower intraocular pressure of an eye. The method comprises the step of providing an opening into an anterior chamber of the eye. A first instrument is inserted into the anterior chamber through the opening. The first instrument is used to perform a surgical procedure other than for lowering intraocular pressure. The first instrument is removed from the anterior chamber. A second instrument is inserted into the anterior chamber through the opening. The second instrument is used to perform a surgical procedure for lowering intraocular pressure. The second instrument is removed from the anterior chamber.

In accordance with another embodiment, a method is provided of performing surgery to lower intraocular pressure of an eye. The method comprises the step of providing an opening into an anterior chamber of the eye. A first instrument is inserted into the anterior chamber through the opening. The first instrument is used to perform a surgical procedure other than for lowering intraocular pressure. The first instrument is removed from the anterior chamber. A second instrument is inserted into the anterior chamber through the opening. The second instrument is used to implant a seton in a trabecular meshwork of the eye such that the seton conducts fluid from the anterior chamber to Schlemm's canal of the eye to lower intraocular pressure. The second instrument is removed from the anterior chamber without removing the seton from the trabecular meshwork.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which.

DETAILED DESCRIPTION OF THE PREFERRED EMBODIMENTS

The preferred embodiments of the invention described herein relate particularly to a surgical treatment of cataract in combination with a surgical and therapeutic treatment of glaucoma through maintaining normal intraocular pressure. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein and below.

Figure 1:
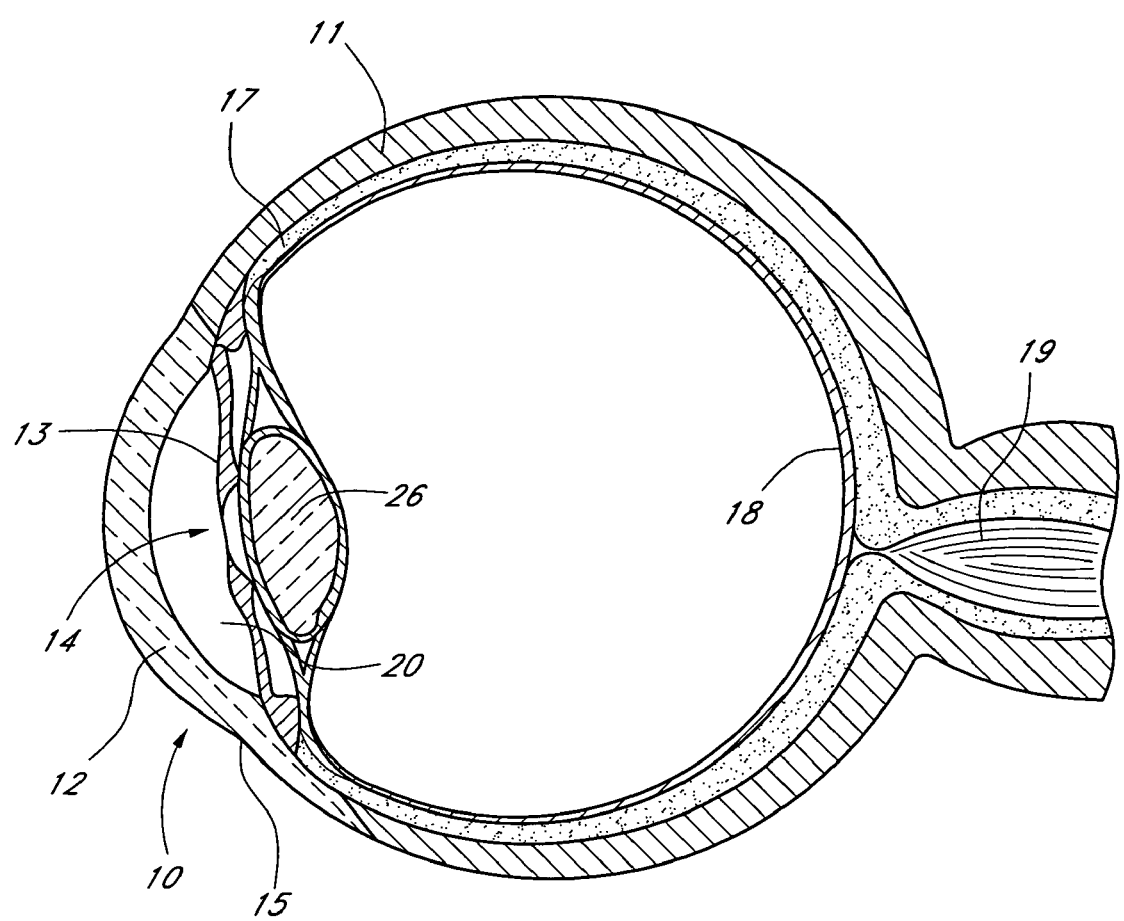
FIG. 1 is a coronal, cross-sectional view of an eye.
Figure 2:
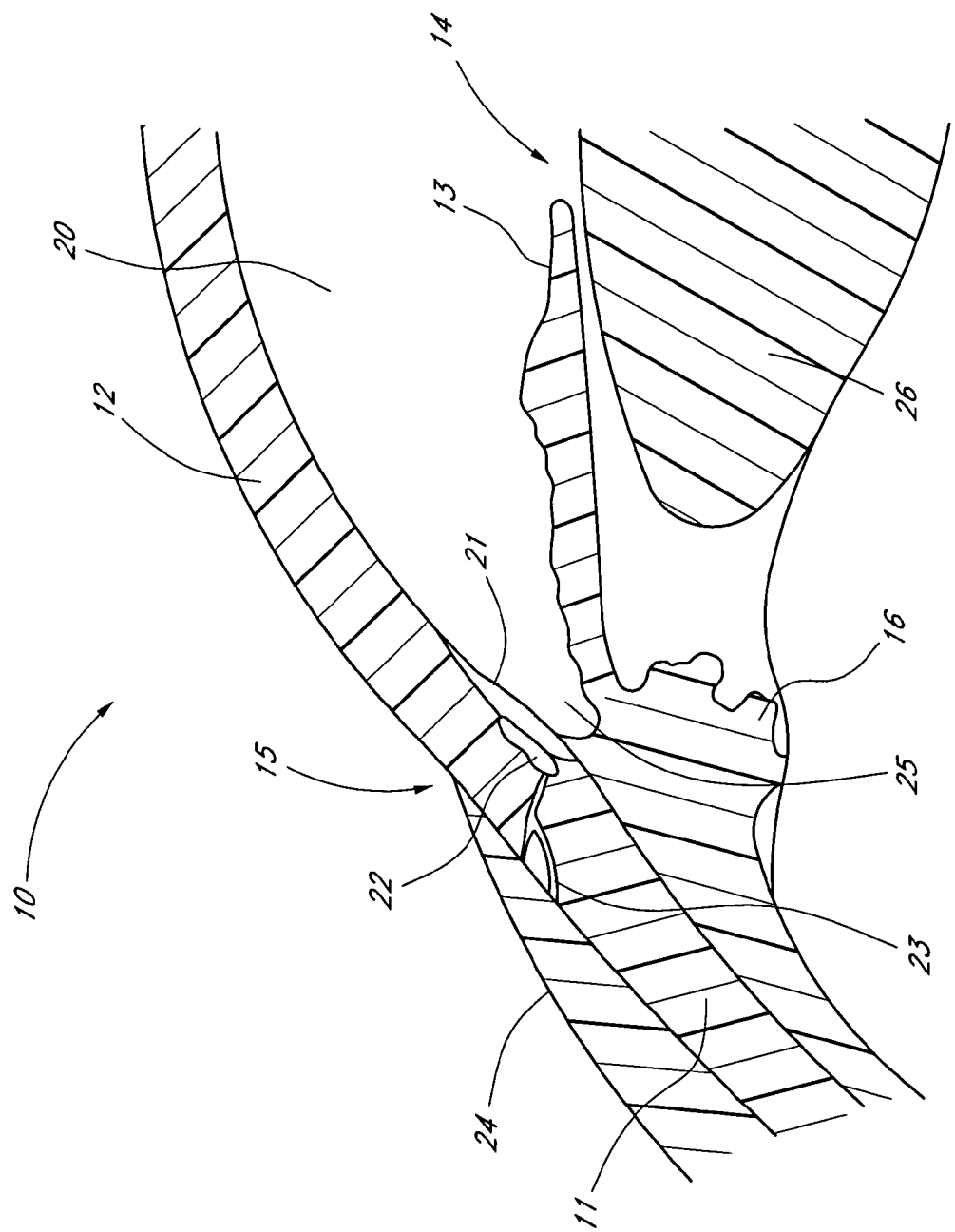
FIG. 2 is an enlarged cross-sectional view of an anterior chamber angle of the eye of FIG. 1.

FIG. 1 is a cross-sectional view of an eye 10, while FIG. 2 is a close-up view showing the relative anatomical locations of a trabecular meshwork 21, an anterior chamber 20, and a Schlemm's canal 22. A sclera 11 is a thick collagenous tissue which covers the entire eye 10 except a portion which is covered by a cornea 12. The cornea 12 is a thin transparent tissue that focuses and transmits light into the eye and through a pupil 14, which is a circular hole in the center of an iris 13 (colored portion of the eye). The cornea 12 mergers into the sclera 11 at a juncture referred to as a limbus 15. A ciliary body 16 extends along the interior of the sclera 11 and is coextensive with a choroid 17. The choroid 17 is a layer of the eye 10, located between the sclera 11 and a retina 18. An optic nerve 19 transmits visual information to the brain and is the anatomic structure that is progressively destroyed by glaucoma.

The anterior chamber 20 of the eye 10 (FIGS. 1 and 2), which is bound anteriorly by the cornea 12 and posteriorly by the iris 13 and a lens 26, is filled with aqueous humor (also herein referred to as "aqueous"). Aqueous is produced primarily by the ciliary body 16, then moves anteriorly through the pupil 14 and reaches an anterior chamber angle 25, formed between the iris 13 and the cornea 12.

Referring in particular to FIGS. 1 and 2, in a normal eye, aqueous is removed from the anterior chamber 20 through the trabecular meshwork 21. Aqueous passes through the trabecular meshwork 21 into Schlemm's canal 22 and thereafter through a plurality of aqueous veins 23, which merge with blood-carrying veins, and into systemic venous circulation. Intraocular pressure (IOP) is maintained by an intricate balance between secretion and outflow of aqueous in the manner described above. Glaucoma is, in most cases, characterized by an excessive buildup of aqueous in the anterior chamber 20 which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery, as compared to surgery for implanting a device, as described herein, which ultimately resides entirely within the confines of the sclera 11 and cornea 12. As discussed in greater detail below, in accordance with some embodiments, a trabecular stenting device is utilized for establishing an outflow pathway, passing through the trabecular meshwork 21.

Trabecular Stenting Device for Reducing Intraocular Pressure (IOP)

Figure 3:
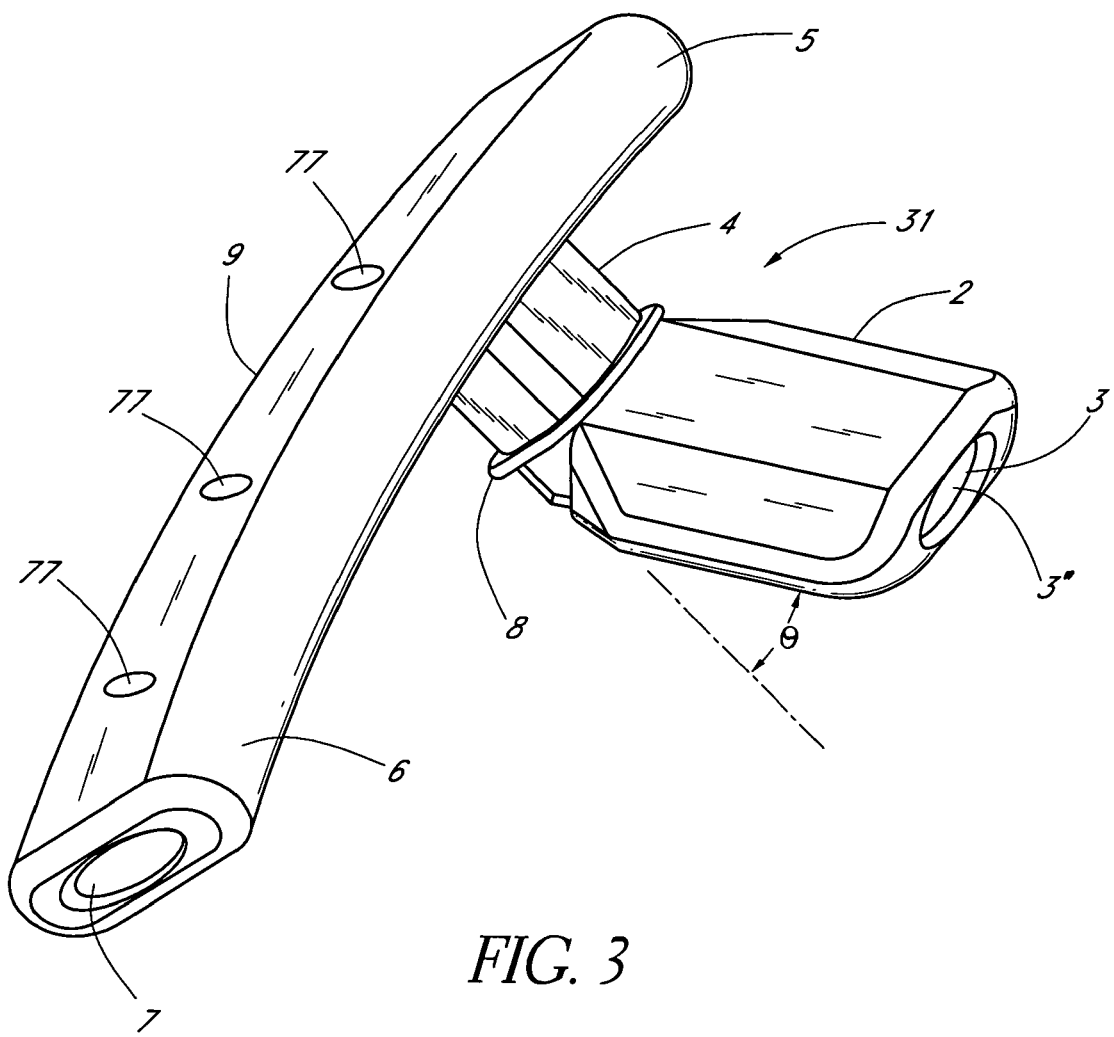
FIG. 3 is an oblique elevation view of a trabecular stent device having features and advantages in accordance with one embodiment of the invention.

FIG. 3 illustrates one preferred embodiment of a trabecular stenting device 31 which facilitates the outflow of aqueous from the anterior chamber 20 into Schlemm's canal 22, and subsequently into the aqueous collectors and the aqueous veins so that intraocular pressure (IOP) is reduced. In the illustrated embodiment, the trabecular stenting device 31 comprises an inlet section 2, having a lumen 3" with an inlet opening 3, a middle section 4, and an outlet section 9.

Referring to FIG. 3, the middle section 4 may be an extension of, or may be coextensive with, the inlet section 2. The outlet section 9 is preferably somewhat flexible to facilitate positioning of the outlet section 9 within an outflow pathway of the eye 10. The outlet section 9 is preferably substantially perpendicular to the middle section 4. "Substantially perpendicular," as used herein, is generally defined as subtending an angle between longitudinal axes of the sections 4, 9 ranging between about 30° (degrees) and about 150° (degrees). The device 31 further comprises at least one lumen 7 within sections 4 and 9 which is in fluid communication with the inlet opening 3 (and/or lumen 3") of section 2, thereby facilitating transfer of aqueous through the device 31.

The trabecular stenting device 31 (FIG. 3) of the preferred embodiments may be made of a biocompatible titanium material or titanium-containing alloy, such as Nitinol. In accordance with one aspect, the trabecular stent is coated with a compound having properties of anticoagulant, antiplatelet, antifibrin and antithrombus that is selected from a group consisting of heparin, wafarin, hirudin, heparinoid, argatroban, forskplin, vapiprost, prostacyclin, dextran, dipyridamole, thrombin inhibitor, and combinations thereof.

As shown in FIG. 3, the outlet section 9 preferably has a first outlet end 6 and a second, opposite outlet end 5. The lumen 7 within the outlet section 9 opens to at least one of the outlet ends 5, 6. Furthermore, the outlet section 9 may have a plurality of side openings 77, each of which is in fluid communication with the lumen 7, for transmission of aqueous. The middle section 4 is connected to or coextensive with the outlet section 9 and is disposed between the first outlet end 6 and the second outlet end 5.

In one preferred embodiment, the outlet section 9 (FIG. 3) is curved around a point, or curve center, and the middle section 4 extends substantially along a plane that contains the curve center. In this embodiment, the outlet section 9 has a radius of curvature ranging between about 4 millimeters (mm) and about 10 mm.

Referring in particular to FIG. 3, as will be apparent to a person skilled in the art, the lumen 7 and the remaining body of the outlet section 9 may have a cross-sectional shape that is oval, circular, or other appropriate shape. The cross-sectional shapes of the lumen 7 and the outlet section 9 preferably conform to the shape of the outflow pathway into which the outlet section 9 is placed. The opening of the lumen 7 of the outlet ends 5, 6 may be ovoid in shape to match the contour of Schlemm's canal 22. Further, an outer contour of the outlet section 9 may be elliptical (e.g., ovoid) in shape to match the contour of Schlemm's canal 22. This serves to minimize rotational movement of the outlet section 9 within Schlemm's canal 22, and thereby stabilizes the inlet section 2 with respect to the iris and cornea.

In the illustrated embodiment of FIG. 3, a circumferential ridge 8 is provided at the junction of the inlet section 2 and the middle section 4 to facilitate stabilization of the device 31 once implanted within the eye 10. Preferably, the middle section 4 has a length (between the ridge 8 and the outlet section 9) that is roughly equal to a thickness of the trabecular meshwork 21, which typically ranges between about 100 microns or micrometers (μm) and about 300 μm. In addition, the outlet section 9 may advantageously be formed with a protuberance or spur projecting therefrom so as to further stabilize the device 31 within the eye 10 without undue suturing.

Figure 4:
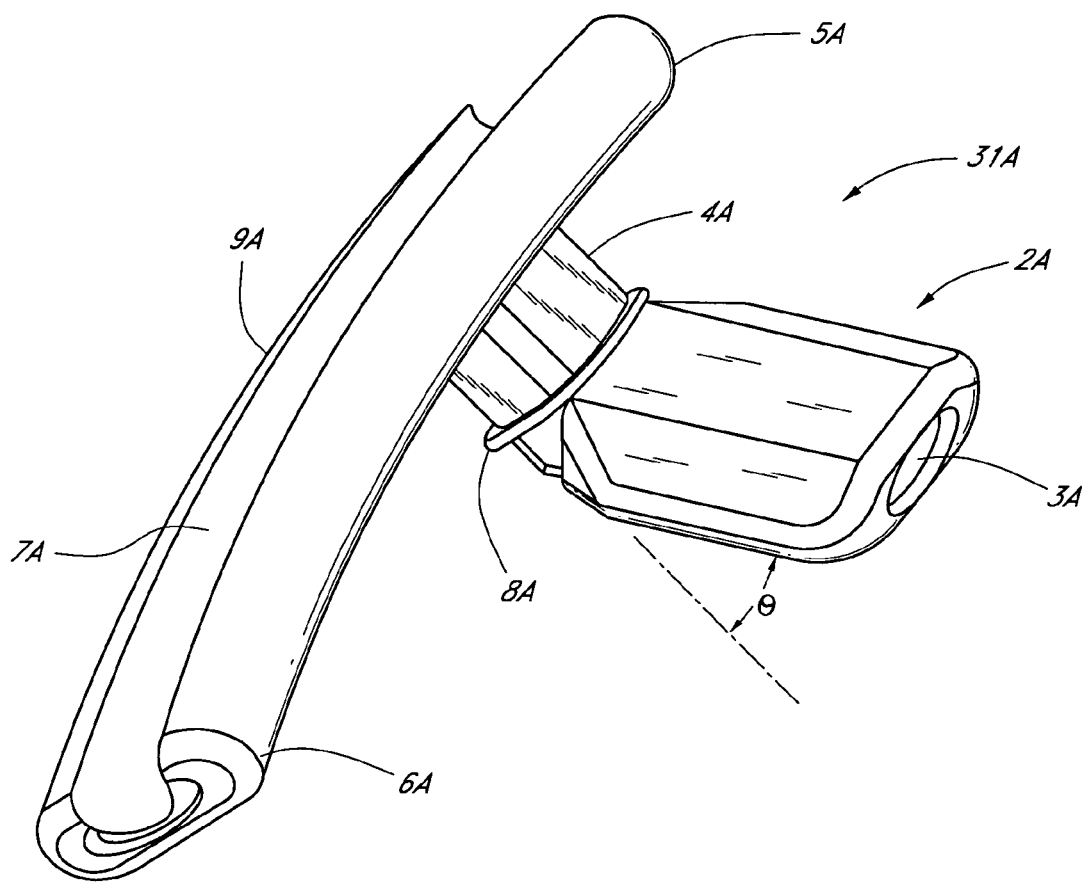
FIG. 4 is an oblique elevation view of a trabecular stent device having features and advantages in accordance with another embodiment of the invention.

FIG. 4 illustrates a modified embodiment of a trabecular stent 31A which facilitates the outflow of aqueous from the anterior chamber 20 into Schlemm's canal 22, and subsequently into the aqueous collectors and the aqueous veins so that intraocular pressure is reduced. The device 31 A comprises an inlet section 2A, a middle section 4A, and an outlet section 9A. The device 31A further comprises at least one lumen 3A traversing the sections 2A, 4A, 9A and providing fluid communication therebetween. The lumen 3A facilitates the transfer of aqueous from the inlet section 2A through the device 31A.

Referring in particular to FIG. 4, the outlet section 9A has opposed ends 5A, 6A. The outlet section 9A is preferably curved, and may also be somewhat flexible, to facilitate positioning of the outlet section 9A within an existing outflow pathway of the eye 10. The outlet section 9A further comprises an elongate trough 7A for transmitting, or venting, aqueous. The elongate trough 7A is connected to and in fluid communication with the lumen 3A within the trabecular stenting device 31A.

In the illustrated embodiment of FIG. 4, a circumferential ridge 8A is provided at the junction of the inlet section 2A and the middle section 4A to facilitate stabilization of the device 31A once implanted within the eye 10. Preferably, the middle section 4A has a length (between the ridge 8A and the outlet section 9A) that is roughly equal to the thickness of the trabecular meshwork 21, which typically ranges between about 100 μm and about 300 μm. In addition, the outlet section 9A may advantageously be formed with a protuberance or barb projecting therefrom so as to further stabilize the device 31A within the eye 10 without undue suturing.

As will be appreciated by those of ordinary skill in the art, the devices 31 (FIG. 3) and 31A (FIG. 4) may advantageously be practiced with a variety of sizes and shapes without departing from the scope of the invention. Depending upon the distance between the anterior chamber 20 and the drainage vessel (e.g., a vein) contemplated, the devices 31, 31A may have a length ranging from about 0.05 centimeters (cm) to over 10 centimeters (cm). Preferably, the devices 31 and 31A have an outside diameter ranging between about 30 μm and about 500 μm, with the lumens 7, 3A having diameters ranging between about 20 μm and about 250 μm, respectively. In addition, the devices 31, 31A may have a plurality of lumens to facilitate transmission of multiple flows of aqueous.

Still referring in particular to FIGS. 3 and 4, the inlet sections 2, 2A have longitudinal axes that form an angle θ ranging between about 20° (degrees) and about 150° (degrees) relative to the longitudinal axes of the middle sections 4, 4A, respectively. More preferably, the angles θ between the longitudinal axes of the inlet sections 2, 2A and the middle sections 4, 4A range between about 30° (degrees) and about 60° (degrees), respectively.

Figure 5:
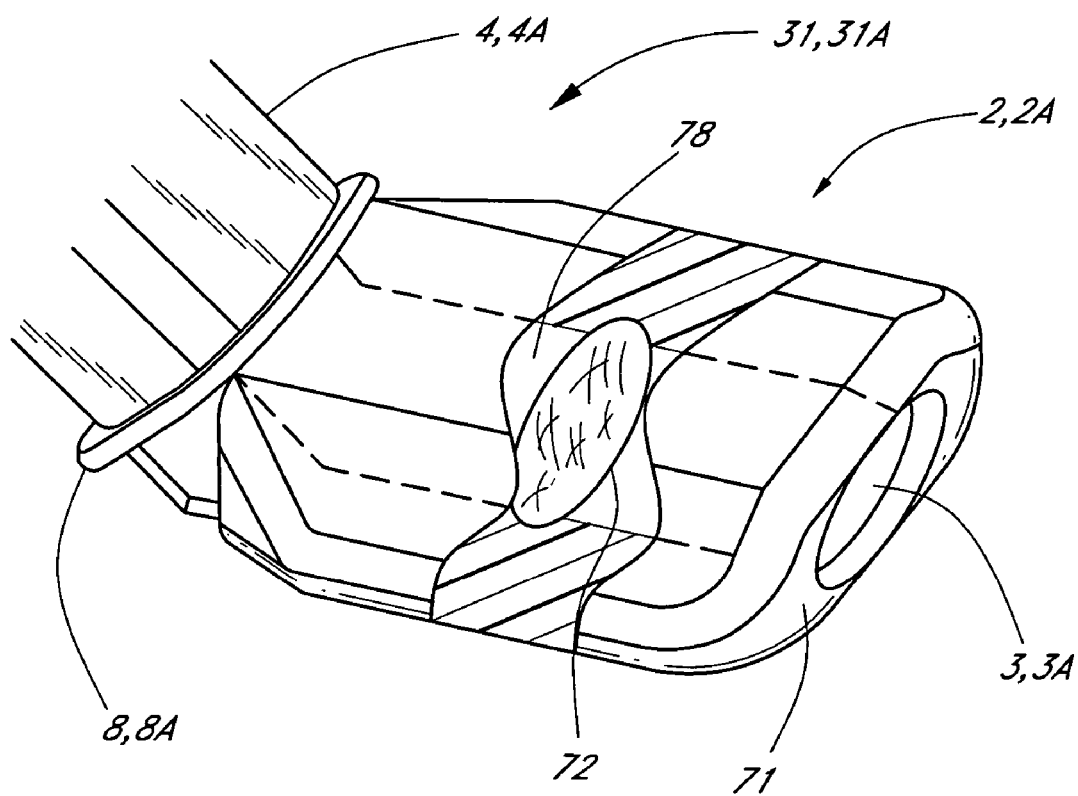
FIG. 5 is a close-up, cut-away view of an inlet section of the trabecular stent device of FIGS. 3 and 4, illustrating a flow-restricting member retained within a lumen of the trabecular stent device and having features and advantages in accordance with another embodiment of the invention.

FIG. 5 is a close-up view of the inlet section 2 and/or 2A of the trabecular stenting device 31 and/or 31A, illustrating a flow-restricting member 72 which is tightly retained within a lumen 78 (or 3"). In the illustrated embodiment, the flow-restricting member 72 is shown located close to an inlet side 71 of the inlet section 2 and/or 2A. The flow-restricting member 72 serves to selectively restrict at least one component in blood from moving retrograde, i.e., from the outlet section 9 (FIG. 3) and/or 9A (FIG. 4) into the anterior chamber 20 of the eye 10.

In modified embodiments, the flow-restricting member 72 (FIG. 5) may be situated in any location within the device 31 and/or 31A such that blood flow is restricted from retrograde motion. More than one flow-restricting member 72 mat also be efficaciously used, as needed or desired. The flow-restricting member 72 may, in some embodiments, be a filter made of a material selected from the following filter materials: expanded polytetrafluoroethylene, cellulose, ceramic, glass, Nylon, plastic, and fluorinated material such as polyvinylidene fluoride ("PVDF") (trade name: Kynar, by DuPont), and combinations thereof.

The trabecular stenting devices 31 (FIG. 3) and/or 31A (FIG. 4) may be made by molding, thermo-forming, or other micro-machining techniques, among other techniques. The trabecular stenting devices 31, 31A preferably comprise a biocompatible material such that inflammation arising due to irritation between the outer surface of the device 31, 31A and the surrounding tissue is minimized.

Biocompatible materials which may be used for the devices 31 (FIG. 3) and/or 31A (FIG. 4) preferably include, but are not limited to, titanium, medical grade silicone, e.g., Silastic™, available from Dow Corning Corporation of Midland, Michigan; and polyurethane, e.g., Pellethane™, also available from Dow Corning Corporation.

In other embodiments, the devices 31 (FIG. 3) and/or 31A (FIG. 4) may comprise other types of biocompatible material, such as, by way of example, polymethylmethacrylate (PMMA), polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other anti-glaucoma drugs, or antibiotics), and the like.

The polymer in accordance with the preferred embodiments should be biocompatible, for example a polymeric material which, in the amounts employed, is non-toxic and chemically inert as well as substantially non-immunogenic and non-inflammatory. Suitable polymeric materials can include, but are not limited to, polycaprolactone (PCL), poly-D,L-lactic acid (DL-PLA), poly-L-lactic acid (L-PLA), poly (lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly (amino acids), cyanoacrylates, poly(trimethylene carbonate), poly(iminocarbonate), copoly(ether-esters), polyalkylene oxalates, polyphosphazenes, polyiminocarbonates, and aliphatic polycarbonates, fibrin, fibrinogen, cellulose, starch, collagen, polyurethane, polyethylene, polyethylene terephthalate, ethylene vinyl acetate, ethylene vinyl alcohol, silicone, polyethylene oxide, polybutylene terephthalate (PBT)-co-PEG, PCL-co-PEG, PLA-co-PEG, polyacrylates, polyoxaesters, polyvinyl pyrrolidone (PVP), polyacrylamide (PAAm), and combinations thereof.

As is well known in the art, a device coated or loaded with a slow-release substance can have prolonged effects on local tissue surrounding the device. The slow-release delivery can be designed such that an effective amount of substance is released over a desired duration. "Substance," as used herein, is generally defined as any therapeutic or active drug that can stop, mitigate, slow-down or reverse undesired disease processes.

In one embodiment, the stent devices 31 (FIG. 3) and/or 31A (FIG. 4) may be made of a biodegradable (also including bioerodible) material admixed with a substance for substance slow-release into ocular tissues. In another embodiment, polymer films may function as substance containing release devices whereby the polymer films may be coupled or secured to the devices 31 and/or 31A. The polymer films may be designed to permit the controlled release of the substance at a chosen rate and for a selected duration, which may also be episodic or periodic. Such polymer films may be synthesized such that the substance is bound to the surface or resides within a pore in the film so that the substance is relatively protected from enzymatic attack. The polymer films may also be modified to alter their hydrophilicity, hydrophobicity and vulnerability to platelet adhesion and enzymatic attack.

Furthermore, the film may be coupled (locally or remotely) to a power source such that when substance delivery is desired, a brief pulse of current is provided to alter the potential on the film to cause the release of a particular amount of the substance for a chosen duration. Application of current causes release of a substance from the surface of the film or from an interior location in the film such as within a pore. The rate of substance delivery is altered depending on the degree of substance loading on the film, the voltage applied to the film, and by modifying the chemical synthesis of substance delivery polymer film.

The power-activated substance delivery polymer film may be designed to be activated by an electromagnetic field, such as, by way of example, Nuclear Magnetic Resonance (NMR), Magnetic Resonance Imaging (MRI), or short range Radio Frequency (RF) transmission (such as Bluetooth). In addition, ultrasound can be used to cause a release of a particular amount of substance for a chosen duration. This is particularly applicable to a substance coated device or a device made of a substrate containing the desired substance.

Exemplary Drug Therapies

The stent devices 31 (FIG. 3) and/or 31A (FIG. 4) may be used for a direct release of pharmaceutical preparations into ocular tissues. As discussed above, the pharmaceuticals may be compounded within the devices 31 and/or 31A or form a coating on the devices 31 and/or 31A. Any known drug therapy for glaucoma may be utilized, including but not limited to, the following.

U.S. Pat. No. 6,274,138 B1, issued Aug. 14, 2001, to Bandman et al. and U.S. Pat. No. 6,231,853 B1, issued May 15, 2001, to Hillman et al., the entire contents of each one of which are hereby incorporated by reference herein, disclose the function of mitochondria and toxic substances synthesized as a metabolic byproduct within mitochondria of cells. Perry and associates (Perry H D et al. "Topical cyclosporin A in the management of postkeratoplasty glaucoma" Cornea 16:284-288, 1997, hereby incorporated by reference herein) report that topical cyclosporin-A has been shown to reduce post-surgical increases in intraocular pressure. It is proposed that such compounds with known effects on mitochondrial stability might be effective in treating trabecular meshwork. An antagonistic drug to neutralize the toxic byproduct or a stabilizing drug to effect mitochondrial stability is believed able to restore the mitochondria function and subsequently mitigate the dysfunction of the trabecular meshwork.

Many types of open angle glaucoma exist; therefore, a number of potential therapeutic mitochondrial interventions may be possible. It is one aspect of the invention to provide a method for stimulating mitochondrial survival/function to prevent demise and secondary apoptosis (that is, programmed cell death). In primary open angle glaucoma, the intraocular pressure increases in response to a decrease in the outflow of aqueous. Research has shown that the number of juxtacanilicular endothelial cells in Schlemm's canal is lower in individuals with glaucoma compared to normals (Grierson I et al., "Age-related changes in the canal of Schlemm" Exp Eye Res, 1984;39(4):505-512, hereby incorporated by reference herein). Since these cells are involved in the energy-dependent egress of aqueous, their demise results in elevated intraocular pressure. Therefore, the mitochondrial treatment objectives for glaucoma preferably include not only the prevention of further endothelial cell death, but also the restoration or boosting of mitochondrial function in the remaining cells. The cells may be made more resilient to elevated intraocular pressure with mitochondrial stimulating therapy by drug slow release. A monoamine oxidase inhibitor, deprenyl, that has been used in the treatment of Parkinson's disease may play a role in reducing neuronal apoptosis in glaucoma; Tatton in U.S. Pat. No. 5,981,598, issued Nov. 9, 1999, the entire contents of which are hereby incorporated by reference herein, states that the primary metabolite of deprenyl, desmethyldeprenyl (DES) is involved in the maintenance of the mitochondrial membrane and prevents apoptotic degradation. It is one aspect of the invention to provide a method for prevention or slowing of apoptotic degradation of optic nerve cells or other cells in trabecular meshwork by administering an effective amount of compounds that energize the mitochondria in the neurons aids the cells by enabling them to better remove compounds that lead to their apoptotic degradation.

U.S. Pat. No. 6,201,001 B1, issued Mar. 13, 2001, to Wang et al., the entire contents of which are hereby incorporated by reference herein, discloses Imidazole antiproliferative agents useful for neovascular glaucoma.

U.S. Pat. No. 6,228,873 B1, issued May 8, 2001, to Brandt et al., the entire contents of which are hereby incorporated by reference herein, discloses a new class of compounds that inhibit function of sodium chloride transport in the thick ascending limb of the loop of Henle, wherein the preferred compounds that are useful are furosemide, piretanide, benzmetanide, bumetanide, torasernide and derivatives thereof.

U.S. Pat. No. 6,194,415 B1, issued Feb. 27, 2001, to Wheeler et al., the entire contents of which are hereby incorporated by reference herein, discloses a method of using quinoxoalines (2-imidazolin-2-ylamino) in treating neural injuries (e.g. glaucomatous nerve damage).

U.S. Pat. No. 6,060,463, issued May 9, 2000, to Freeman and U.S. Pat. No. 5,869,468, issued Feb. 9, 1999, to Freeman, the entire contents of each one of which are hereby incorporated by reference herein, disclose treatment of conditions of abnormally increased intraocular pressure by administration of phosphonylmethoxyalkyl nucleotide analogs and related nucleotide analogs.

U.S. Pat. No. 5,925,342, issued Jul. 20, 1999, to Adorante et al., the entire contents of which are hereby incorporated by reference herein, discloses a method for reducing intraocular pressure by administration of potassium channel blockers.

U.S. Pat. No. 5,814,620, issued Sep. 29, 1998, to Robinson et al., the entire contents of which are hereby incorporated by reference herein, discloses a method of reducing neovascularization and of treating various disorders associated with neovascularization. These methods include administering to a tissue or subject a synthetic oligonucleotide.

U.S. Pat. No. 5,767,079, issued Jun. 16, 1998, to Glaser et al., the entire contents of which are hereby incorporated by reference herein, discloses a method for treatment of ophthalmic disorders by applying an effective amount of Transforming Growth Factor-Beta (TGF-beta or TGF-β) to the affected region.

U.S. Pat. No. 5,663,205, issued Sep. 2, 1997, to Ogawa et al., the entire contents of which are hereby incorporated by reference herein, discloses a pharmaceutical composition for use in glaucoma treatment which contains an active ingredient 5-[1-hydroxy-2-[2-(2-methoxyphenoxyl)ethylamino]ethyl]-2-methylbenzenesulfonamide. This agent is free from side effects, and stable and has an excellent intraocular pressure reducing activity at its low concentrations, thus being useful as a pharmaceutical composition for use in glaucoma treatment.

U.S. Pat. No. 5,652,236, issued Jul. 29, 1997, to Krauss, the entire contents of which are hereby incorporated by reference herein, discloses pharmaceutical compositions and a method for treating glaucoma and/or ocular hypertension in the mammalian eye by administering thereto a pharmaceutical composition which contains as the active ingredient one or more compounds having guanylate cyclase inhibition activity. Examples of guanylate cyclase inhibitors utilized in the pharmaceutical composition and method of treatment are methylene blue, butylated hydroxyanisole and N-methylhydroxylamine.

U.S. Pat. No. 5,547,993, issued Aug. 20, 1996, to Miki, the entire contents of which are hereby incorporated by reference herein, discloses that 2-(4-methylaminobutoxy) diphenylmethane or a hydrate or pharmaceutically acceptable salt thereof have been found useful for treating glaucoma.

U.S. Pat. No. 5,502,052, issued Mar. 26, 1996, to DeSantis, the entire contents of which are hereby incorporated by reference herein, discloses use of a combination of apraclonidine and timolol to control intraocular pressure. The compositions contain a combination of an alpha-2 agonist (e.g., para-amino clonidine) and a beta blocker (e.g., betaxolol).

U.S. Pat. No. 6,184,250 B1, issued Feb. 6, 2001, to Klimko et al., the entire contents of which are hereby incorporated by reference herein, discloses use of cloprostenol and fluprostenol analogues to treat glaucoma and ocular hypertension. The method comprises topically administering to an affected eye a composition comprising a therapeutically effective amount of a combination of a first compound selected from the group consisting of beta-blockers, carbonic anhydrase inhibitors, adrenergic agonists, and cholinergic agonists; together with a second compound.

U.S. Pat. No. 6,159,458, issued Dec. 12, 2000, to Bowman et al., the entire contents of which are hereby incorporated by reference herein, discloses an ophthalmic composition that provides sustained release of a water soluble medicament formed by comprising a crosslinked carboxy-containing polymer, a medicament, a sugar and water.

U.S. Pat. No. 6,110,912, issued Aug. 29, 2000, to Kaufman et al., the entire contents of which are hereby incorporated by reference herein, discloses methods for the treatment of glaucoma by administering an ophthalmic preparation comprising an effective amount of a non-corneotoxic serine-threonine kinase inhibitor, thereby enhancing aqueous outflow in the eye and treatment of the glaucoma. In some embodiments, the method of administration is topical, whereas it is intracameral in other embodiments. In still further embodiments, the method of administration is intracanalicular.

U.S. Pat. No. 6,177,427 B1, issued Jan. 23, 2001, to Clark et al., the entire contents of which are hereby incorporated by reference herein, discloses compositions of non-steroidal glucocorticoid antagonists for treating glaucoma or ocular hypertension.

U.S. Pat. No. 5,952,378, issued Sep. 14, 1999, to Stjernschantz et al., the entire contents of which are hereby incorporated by reference herein, discloses the use of prostaglandins for enhancing the delivery of drugs through the uveoscleral route to the optic nerve head for treatment of glaucoma or other diseases of the optic nerve as well as surrounding tissue. The method for enhancing the delivery to the optic nerve head comprises contacting a therapeutically effective amount of a composition containing one or more prostaglandins and one or more drug substances with the eye at certain intervals.

Trabecular Device Use and Operation

One preferred method for increasing aqueous outflow in the eye 10 (FIGS. 1 and 2) of a patient, to reduce intraocular pressure therein, comprises bypassing the trabecular meshwork 21. Though much of the discussion below refers to the device 31 of FIG. 3, the skilled artisan will readily appreciate that the device 31A of FIG. 4 may be efficaciously utilized in a substantially similar manner.

In operation, the middle section 4 of the device 31 (FIG. 3) is advantageously placed across the trabecular meshwork 21 through a slit or opening. This opening can be created by using a laser, a knife, or other suitable surgical cutting instrument. The opening may advantageously be substantially horizontal, i.e., extending longitudinally in the same direction as the circumference of the limbus 15 (FIG. 2). Other opening directions may also be efficaciously used, as needed or desired. The opening may advantageously be oriented at any angle, relative to the circumference of the limbus 15, that is appropriate for inserting the device 31 through the trabecular meshwork 21 and into Schlemm's canal 22 or other outflow pathway, as will be apparent to those skilled in the art.

Referring in particular to FIG. 3, the middle section 4 may be semi-flexible and/or adjustable in position relative to the inlet section 2 and/or the outlet section 9, further adapting the device 31 for simple and safe glaucoma implantation. Furthermore, the outlet section 9 may be positioned into fluid collection channels of the natural outflow pathways. Such natural outflow pathways include Schlemm's canal 22, aqueous collector channels, aqueous veins, and episcleral veins. The outlet section 9 may be positioned into fluid collection channels up to at least the level of the aqueous veins, with the device inserted in a retrograde or antegrade fashion.

Figure 6:
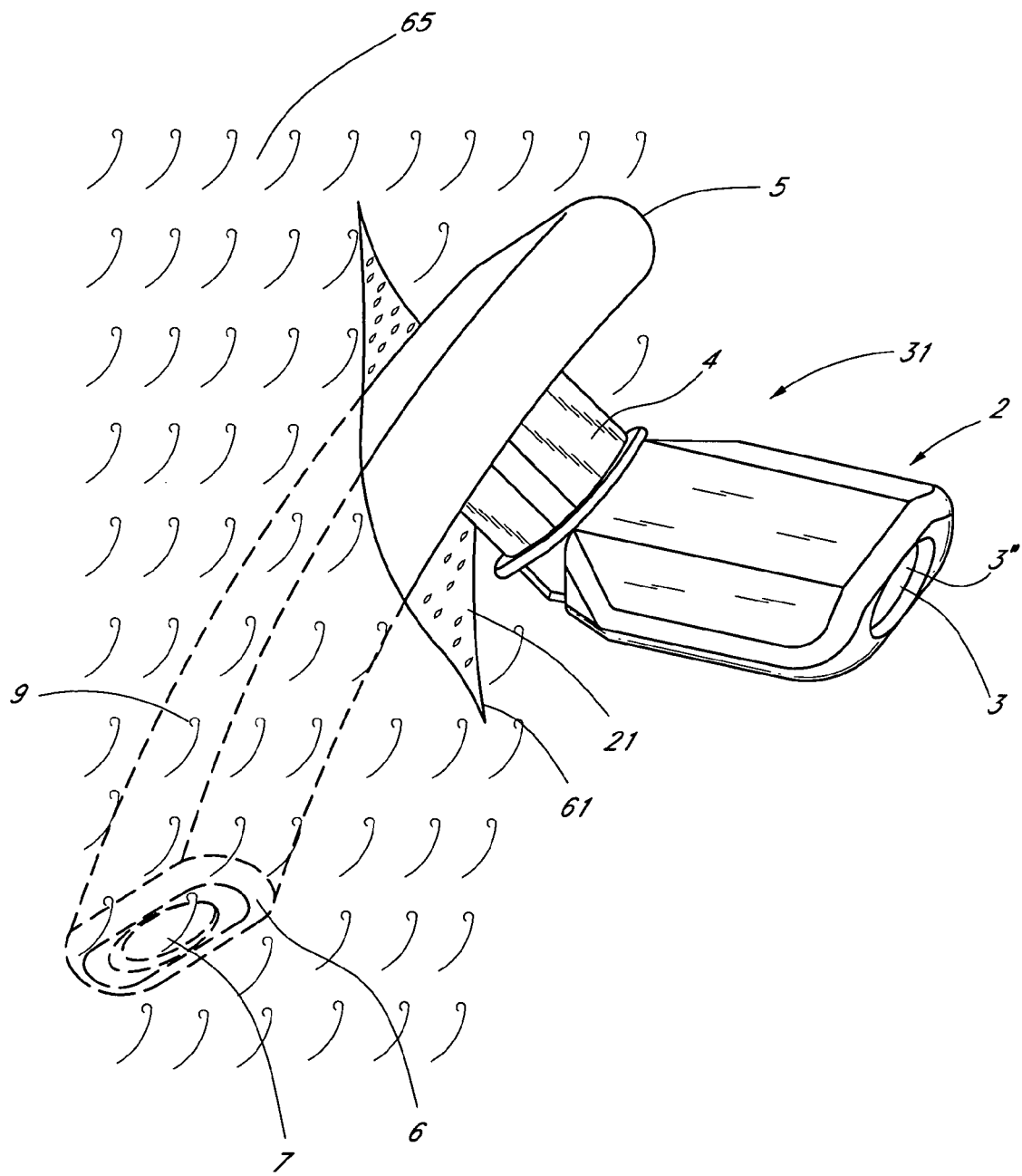
FIG. 6 is an oblique elevation view illustrating the placement of one end of the trabecular stent device of FIG. 3 through a trabecular meshwork in accordance with one embodiment of the invention.

FIG. 6 generally illustrates one step in the implantation of the trabecular stenting device 31 through the trabecular meshwork 21. The outlet section 9 of the device 31 is inserted into an opening 61 in the trabecular meshwork 21. A practitioner or surgeon may create the opening 61 "ab interno" from the interior surface 65 of the trabecular meshwork 21. The practitioner then advances the first outlet end 6 of the outlet section 9 through the opening 61 into a first side of Schlemm's canal 22 or other suitable outflow pathway within the eye 10. Next, the practitioner advances the second outlet end 5 through the opening 61 and into a second side of Schlemm's canal 22. The advancing of the second outlet end 5 may be facilitated by slightly pushing the second outlet end 5 through the opening 61.

Figure 7:
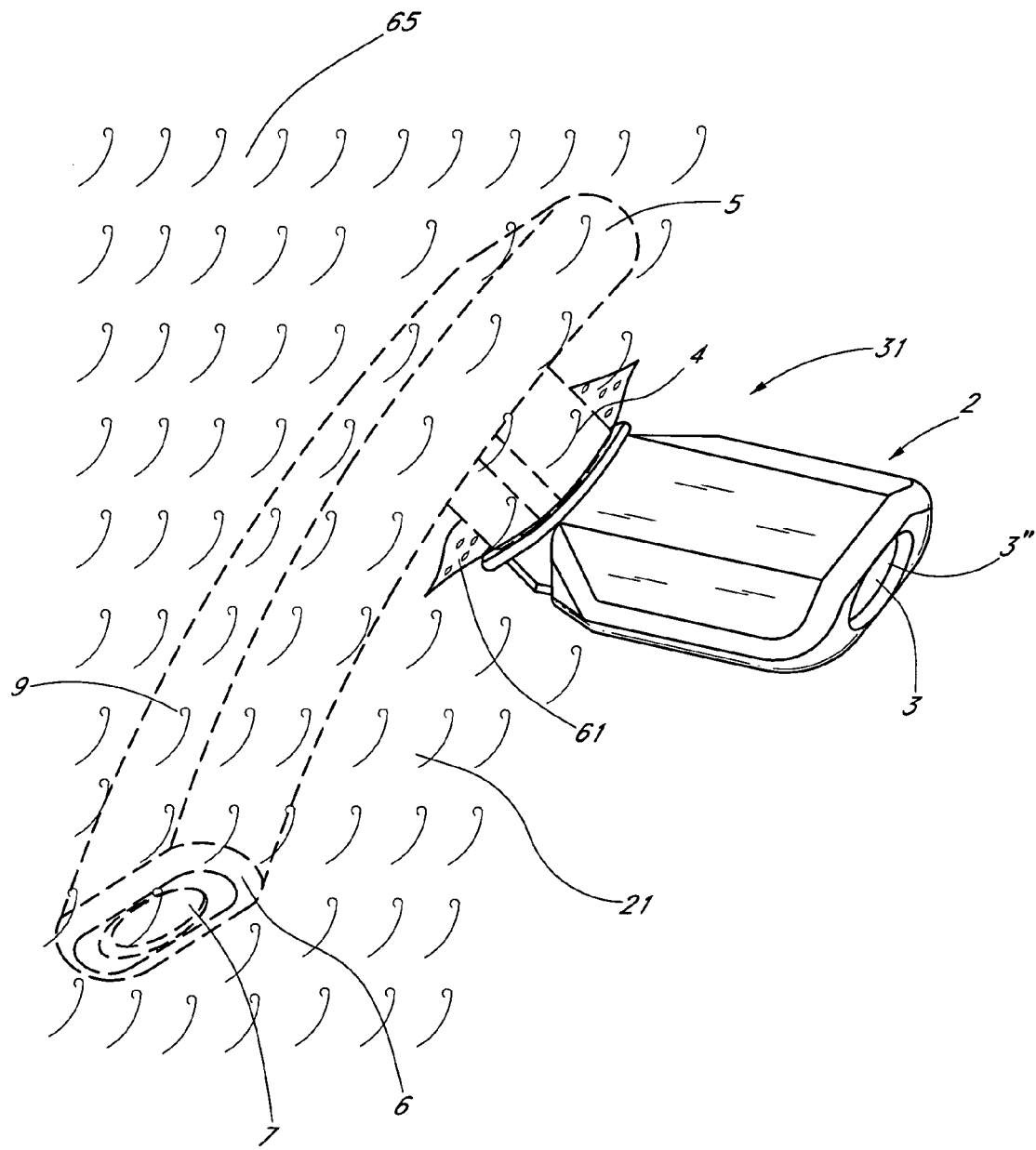
FIG. 7 is an oblique elevation view of a preferred implantation of the trabecular stent device of FIG. 3 through a trabecular meshwork in accordance with one embodiment of the invention.

FIG. 7 generally illustrates a further stage in deployment of the device 31, wherein the entire outlet section 9 of the device 31 is implanted within Schlemm's canal 22, beneath the trabecular meshwork 21. At this stage, the lumen 3" (or inlet opening 3) of the implanted device 31 provides an enhanced fluid communication through the trabecular meshwork 21 and between the anterior chamber 20 (FIGS. 1 and 2) and Schlemm's canal 22.

Figure 8:
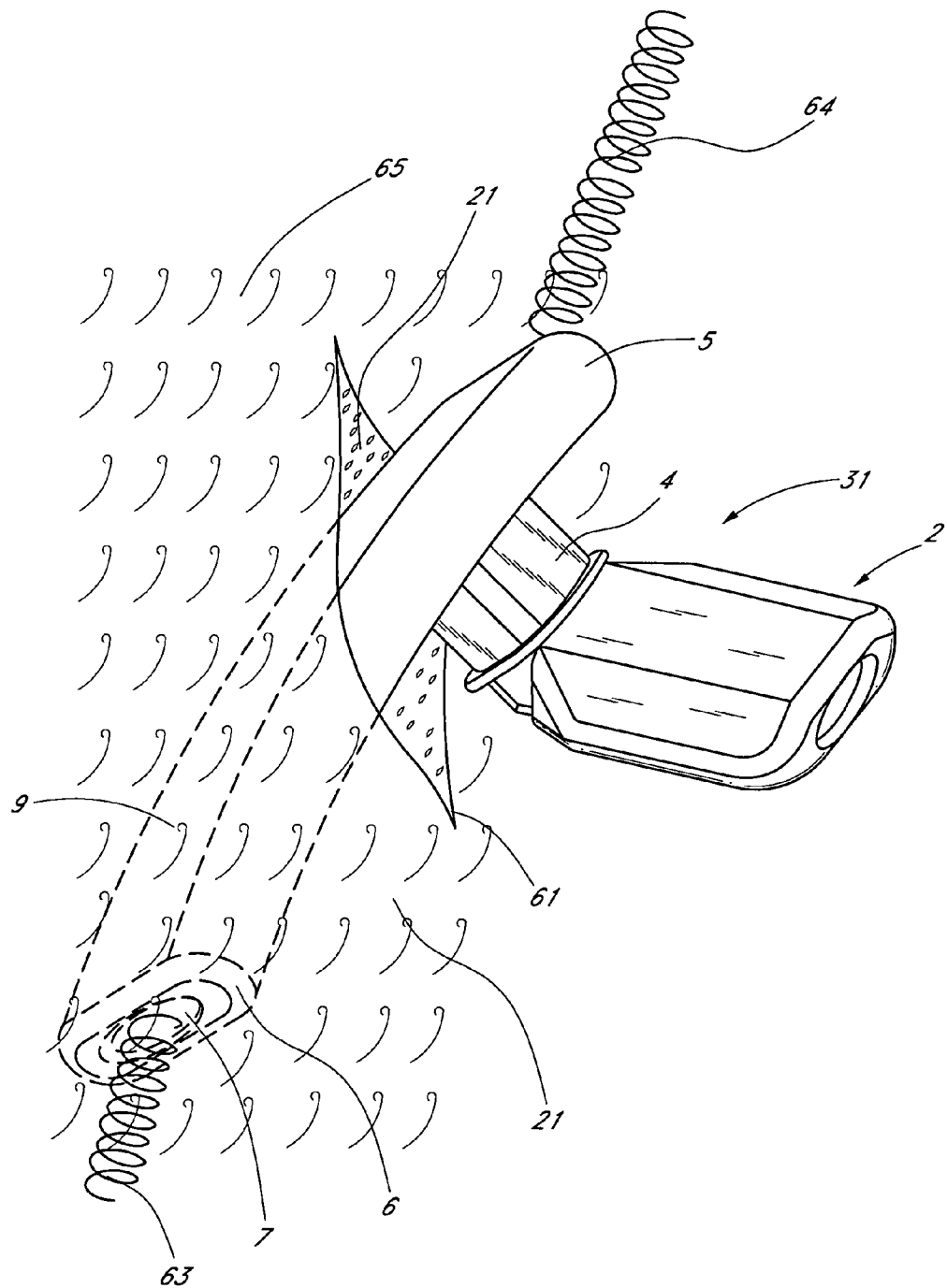
FIG. 8 is an oblique elevation view illustrating the placement of one end of the trabecular stent device of FIG. 3 through a trabecular meshwork, wherein the trabecular stent device is passed over a guidewire, in accordance with one embodiment of the invention.

FIG. 8 shows an additional and/or modified step in the implantation of the trabecular stenting device 31 through the trabecular meshwork 21. The practitioner inserts a distal end 63 of a guidewire 64 through the opening 61 into the first side Schlemm's canal 22. The practitioner then advances the first outlet end 6 of the outlet section 9 into Schlemm's canal 22 by "riding," or advancing, the trabecular stenting device 31 on the guidewire 64. As will be apparent to those skilled in the art, the guidewire 64 will have a shape and size conforming to the shape and size of the lumen 7; and as such, may have an elliptical (e.g., oval) shape, a D-shape, a round shape, or an irregular (asymmetric) shape which is adapted for nonrotatory engagement with or for the device 31.

One method for increasing aqueous outflow within the eye 10 of a patient, and thus reduce intraocular pressure therein, comprises: (a) creating an opening in the trabecular meshwork 21, wherein the trabecular meshwork 21 includes a deep side and a superficial side; (b) inserting the trabecular stenting device 31 into the opening; and (c) transmitting aqueous or intraocular liquid through the device 31, to bypass the trabecular meshwork 21, from the deep side to the superficial side of the trabecular meshwork 21. This "transmitting" of aqueous or intraocular liquid is preferably passive, i.e., aqueous or intraocular liquid flows out of the anterior chamber 20 due to a pressure gradient between the anterior chamber 20 and the aqueous venous system 23.

Another method for increasing aqueous outflow within the eye 10 of a patient, and thus reduce intraocular pressure therein, comprises a) providing at least one pharmaceutical substance incorporated into a trabecular stenting device at about the middle section of the device; b) implanting the trabecular stenting device within a trabecular meshwork of an eye such that the middle section is configured substantially within the trabecular meshwork, the stenting device having a first end positioned in an anterior chamber of the eye while a second end is positioned inside a Schlemm's canal, wherein the first and the second ends of the trabecular stenting device establish a fluid communication between the anterior chamber and the Schlemm's canal; and c) allowing the middle section of the trabecular stenting device to release a quantity of said pharmaceutical substance into the trabecular meshwork.

It should be understood that the devices 31 (FIG. 3) and 31A (FIG. 4) are not limited to implantation within only Schlemm's canal 22, as generally depicted by the embodiments of FIGS. 6-8. Rather, the devices 31 and 31A may advantageously be implanted within and/or used in conjunction with a variety of other natural outflow pathways, or biological tubular structures, as mentioned above. As will be apparent to those of ordinary skill in the art, the devices 31 and 31A may advantageously be used in conjunction with substantially any biological tubular structure without detracting from or limiting the scope of the invention.

Figure 9:
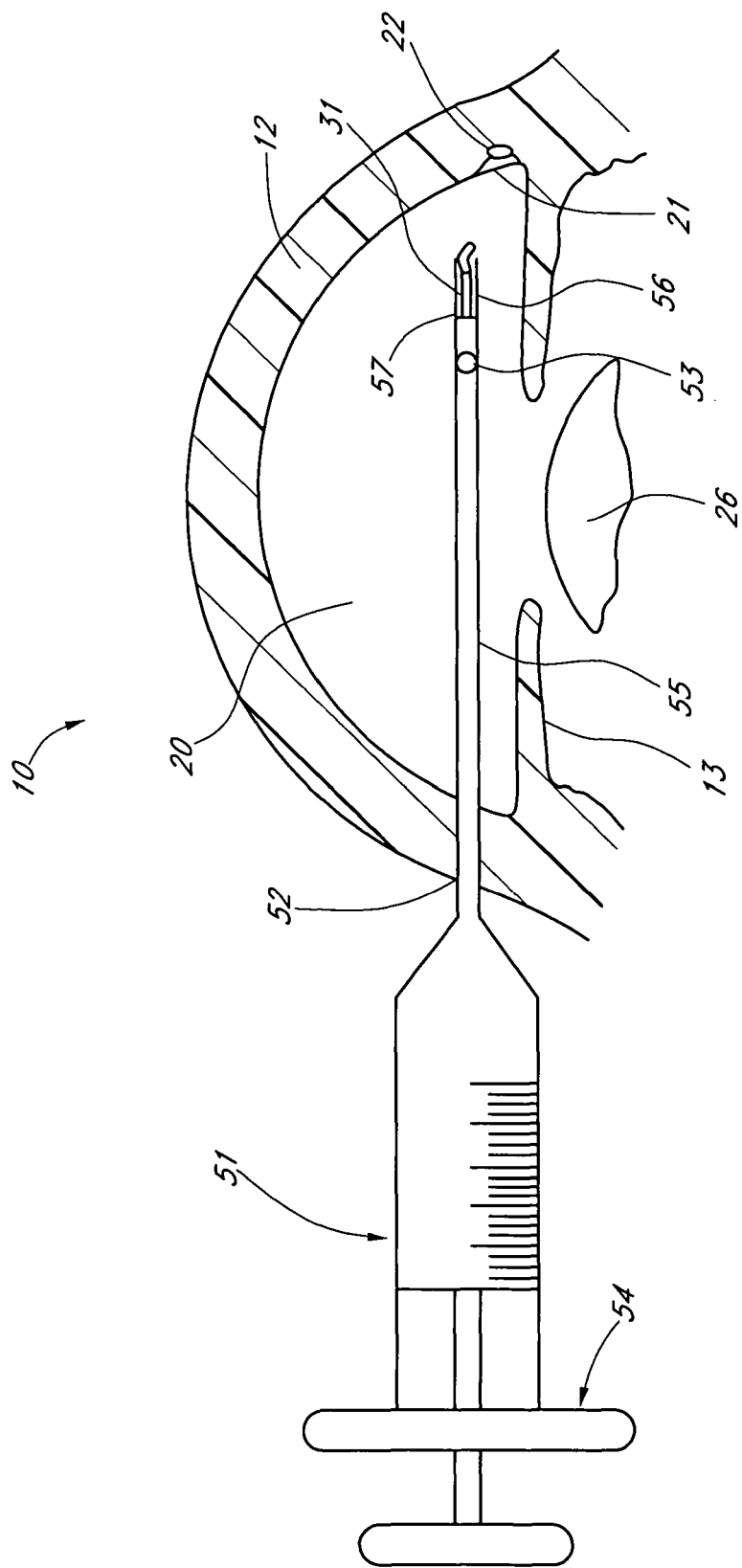
FIG. 9 is an enlarged, cross-sectional view of a preferred method of implanting the trabecular stent device of FIG. 3 within an eye and having features and advantages in accordance with one embodiment of the invention.

FIG. 9 generally illustrates a preferred method by which the trabecular stenting device 31 is implanted within the eye 10. In the illustrated method, a delivery applicator 51 is provided, which preferably comprises a syringe portion 54 and a cannula portion 55 which contains at least one lumen (not shown). The cannula portion 55 preferably has a size of about 30 gauge. However, in other embodiments, the cannula portion 55 may have a size ranging between about 16 gauge and about 40 gauge. A distal section of the cannula portion 55 has at least one irrigating hole 53 in fluid communication with the lumen.

Still referring in particular to FIG. 9, a holder for holding the device 31 comprises a lumen 56 having a proximal end 57. In other embodiments, the holder may advantageously comprise a lumen, a sheath, a clamp, tongs, a space, and the like. The proximal end 57 of the lumen 56 is preferably sealed off from the remaining lumen of the cannula portion 55 and the irrigating hole 53 of the cannula portion 55. As will be recognized by those skilled in the art, however, in other embodiments of the cannula portion 55, the lumen 56 may advantageously be placed in fluid communication with the lumen and irrigating hole 53 of the cannula portion 55 without detracting from or limiting the scope of the invention.

In the method illustrated in FIG. 9, the device 31 is placed into the lumen 56 of the delivery applicator 51 and then advanced to a desired implantation site within the eye 10. The delivery applicator 51 holds the device 31 securely during delivery and releases it when the practitioner initiates deployment of the device 31.

In one preferred embodiment of trabecular meshwork surgery, a patient is placed in a supine position, prepped, draped, and appropriately anesthetized. A small incision 52 (FIG. 9) is then made through the cornea 12. In one embodiment, the incision 52 is made through the cornea 12 near or proximate to the limbus 15 (FIG. 2). In another embodiment, the incision 52 is made substantially at the limbus 15.

The incision 52 (FIG. 9) preferably has a surface length less than about 1.0 millimeters (mm) in length and may advantageously be self-sealing. Through the incision 52, the trabecular meshwork 21 is accessed, wherein an incision is made with an irrigating knife (not shown). The device 31 is then advanced through the corneal incision 52 and across the anterior chamber 20, while the device 31 is held in the delivery applicator 51, under gonioscopic, microscopic, or endoscopic guidance. After the device 31 is appropriately implanted, the applicator 51 is withdrawn and the trabecular meshwork surgery is concluded.

Figure 10:
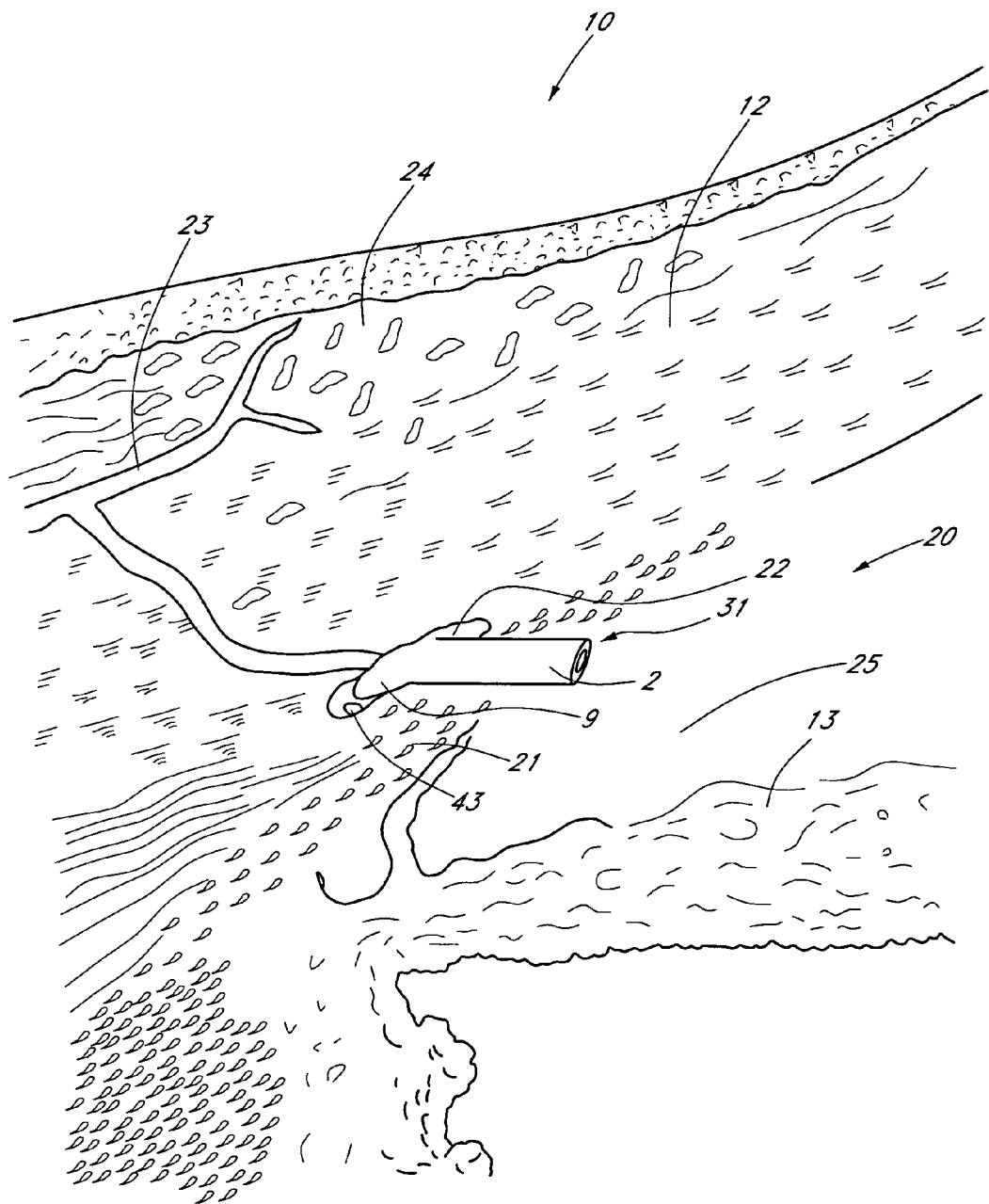
FIG. 10 is a perspective view of an anterior chamber angle of an eye, illustrating the trabecular stent device of FIG. 3 positioned within a trabecular meshwork and having features and advantages in accordance with one embodiment of the invention.

FIG. 10 generally illustrates the use of the trabecular stenting device 31 for establishing an outflow pathway, passing from the anterior chamber 20 through the trabecular meshwork 21 to Schlemm's canal 22. As illustrated, an opening has been created in the trabecular meshwork 21. As will be appreciated by those of ordinary skill in the art, such an opening in the trabecular meshwork 21 may comprise an incision made with a microknife, a pointed guidewire, a sharpened applicator, a screw-shaped applicator, an irrigating applicator, a barbed applicator, and the like. In modified embodiments, the trabecular meshwork 21 may advantageously be dissected with an instrument similar to a retinal pick or microcurrette. Furthermore, the opening may advantageously be created by fiberoptic laser ablation.

Referring again to FIG. 10, the outlet section 9 of the device 31 has been inserted in its entirety into the opening in the trabecular meshwork 21. The inlet section 2 is exposed to the anterior chamber 20, while the outlet section 9 is positioned near an interior surface 43 of Schlemm's canal 22. In other embodiments, the outlet section 9 may advantageously be placed into fluid communication with other natural outflow pathways, such as, but not limited to, aqueous collector channels, aqueous veins, and episcleral veins, as described above. A device such as the device 31A of FIG. 4, wherein the outflow section 9A has an open trough 7A for stenting purposes, may be used to maintain an opening of one or more of such natural outflows pathways. With the trabecular stenting device 31 implanted as illustrated in FIG. 10, aqueous flows from the anterior chamber 20 through the device 31 into Schlemm's canal 22, bypassing the trabecular meshwork 21, thereby reducing intraocular pressure within the eye 10.

A number of devices and methods for treating glaucoma and/or reducing intraocular pressure (IOP) may be utilized in conjunction with the preferred embodiments. For example, a seton generally comprising a tubular member or tube with opposed open ends may be used in trabecular meshwork surgery to provide an outflow pathway for intraocular liquid to lower IOP. In cases, where temporary lowering of IOP is desired, for example, during surgery other than that for glaucoma or chronic high IOP, an incision or opening may be created in the trabecular meshwork to provide an outflow pathway for intraocular liquid to temporarily lower IOP during surgery. This incision may then "fill in" over time to restore the trabecular meshwork to its normal state.

The following co-pending patent applications disclose devices and methods for treating glaucoma and/or reducing intraocular pressure (IOP), among other things, the entire contents of each one of which are hereby incorporated by reference herein:

U.S. application Ser. No. 09/549,350, filed Apr. 14, 2000, entitled APPARATUS AND METHOD FOR TREATING GLAUCOMA;

U.S. application Ser. No. 09/596,781, filed Jun. 19, 2000, entitled STENTED TRABECULAR SHUNT AND METHODS THEREOF;

U.S. application Ser. No. 09/704,276, filed Nov. 1, 2000, entitled GLAUCOMA TREATMENT DEVICE;

U.S. application Ser. No. 09/847,523, filed May 2, 2001, entitled BIFURACATABLE TRABECULAR SHUNT FOR GLAUCOMA TREATMENT;

U.S. application Ser. No. 10/046,137, filed Nov. 8, 2001, entitled DRUG RELEASING TRABECULAR IMPLANT FOR GLAUCOMA TREATMENT;

U.S. application Ser. No. 10/101,548, filed Mar. 18, 2002, entitled APPLICATOR AND METHODS FOR PLACING A TRABECULAR SHUNT FOR GLAUCOMA TREATMENT;

U.S. application Ser. No. 10/118,578, filed Apr. 8, 2002, entitled GLAUCOMA STENT AND METHODS THEREOF FOR GLAUCOMA TREATMENT;

U.S. application Ser. No. 10/137,117, filed May 1, 2002, entitled GLAUCOMA DEVICE AND METHODS THEREOF; and U.S. application Ser. No. 10/139,800, filed May 3, 2002, entitled MEDICAL DEVICE AND METHODS OF USE FOR GLAUCOMA TREATMENT.

Cataract Surgery

Figure 11:
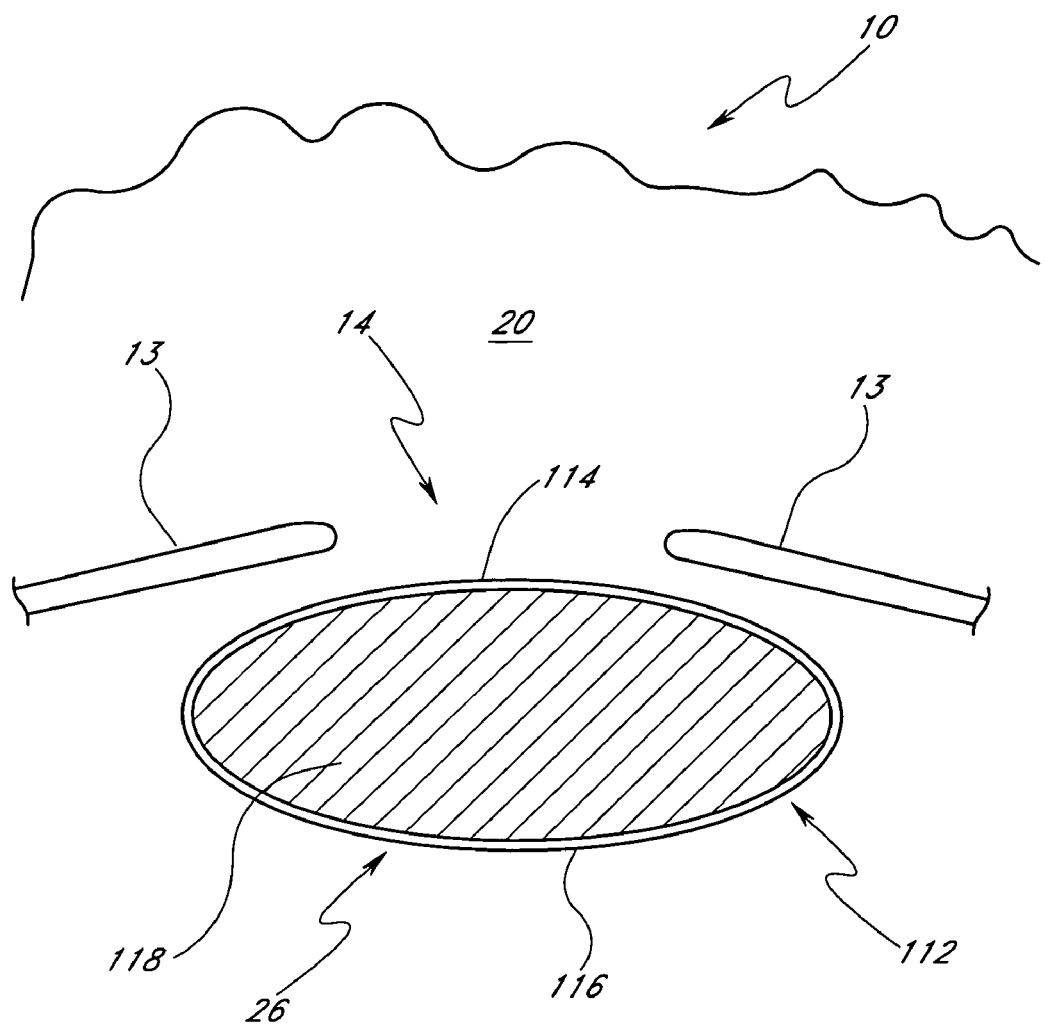
FIG. 11 is a simplified schematic view of a lens of an eye.
Figure 11:

Referring in particular to FIG. 11, the transparency of the lens 26 of the eye 10 generally depends on the physiochemical state of the lens proteins. These proteins, like the proteins of other organs, are sensitive to changes in the properties of their surrounding fluid. Changes in the concentration of dissolved salts, in the osmotic pressure, in the pH or in the enzyme activity of the surrounding fluid can alter the properties of the lens proteins. Also, like other organs, changes to the proteins of the lens occur with age. A common type of cataract that occurs in elderly people is known as a senile cataract. This type of cataract has no known etiology and none of the forms of cataract produced experimentally to date closely resemble the senile cataract.

Still referring to FIG. 11, the lens 26 of the human eye 10 is a crystalline lens that generally comprises an outer capsule 112 with anterior and posterior surface 114, 116, the lens 26 containing a clear central matrix 118. This central matrix 118 often opacifies with age and for various other reasons (some of which have been mentioned above) and thereby progressively blocks the passage of light to the retina 18 of the eye 10. Eventually, the central matrix 118 attains a degree of opacity which is referred to as a cataract. This abnormal ocular condition is corrected by removing the opacacified lens, which is a procedure known as cataract extraction, and replacing the lens by an artificial lens for focusing the light entering the eye 10 on the retina 18. Intraocular lenses have gained widespread acceptance as replacements for cataracted human lenses.

Artificial intraocular lenses generally comprise an optical region and a support, or haptic, to facilitate positioning and centering of the intraocular lens within the eye. Intraocular lenses have been made from a number of different materials. For example, hard lenses have been prepared from polymethylmethacrylate (PMMA) and optical glass while flexible lenses have been prepared from silicone, polyHEMA (polyhyroxyethylmethymethacrylate), acrylics, collagen, and combinations thereof. Flexible lenses have the advantage that they can be folded or otherwise deformed prior to implantation to reduce the overall size of the lens during the artificial lens implantation procedure through an incision in the cornea or limbus. As discussed above and further below, this small incision enables placement of a glaucoma stent passing the anterior chamber into a trabecular meshwork opening.

Artificial intraocular lenses are generally categorized as anterior chamber intraocular lenses and posterior chamber intraocular lenses depending on the implant locations. For example, Leiske in U.S. Pat. No. 4,560,383, the entire contents of which are hereby incorporated by reference herein, discloses several embodiments of an anterior chamber intraocular lens that can be utilized in both primary and secondary implantations with either intracapsular or extracapsular cataract extractions. The lens is made of PMMA material that is low-mass, low-weight with reduced possibility of reaction and internal stress due to eye movement or sudden movement.

Figure 12:
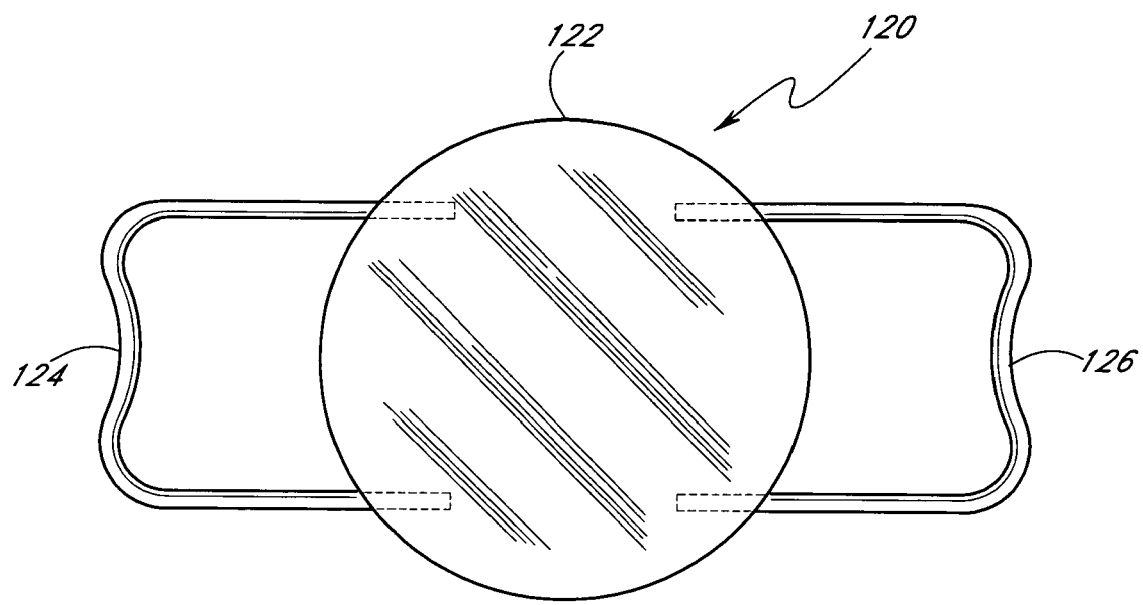
FIG. 12 is a top plan view of one embodiment of an anterior chamber intraocular lens.
Figure 13:
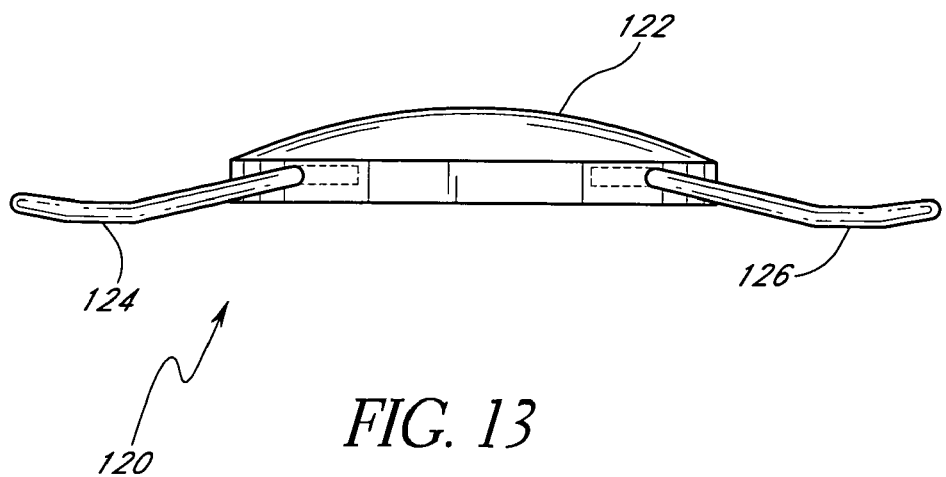
FIG. 13 is a side view of the intraocular lens of FIG. 12.

FIGS. 12 and 13 show different views of one embodiment of an anterior chamber intraocular lens device 120. The lens 120 generally comprises a lens optic 122 and a pair of flexible opposing loops 124, 126 secured into a side edge of the optic 122.

Further, for example, Faulkner in U.S. Pat. No. 4,366,582, the entire contents of which are hereby incorporated by reference herein, discloses several embodiments of a posterior chamber intraocular lens. Faulkner's lens is provided with a structure for engaging the anterior surface of the iris to retain the lens against posterior displacement within the eye, even if the capsule is missing or damaged.

Figures 14, 15:
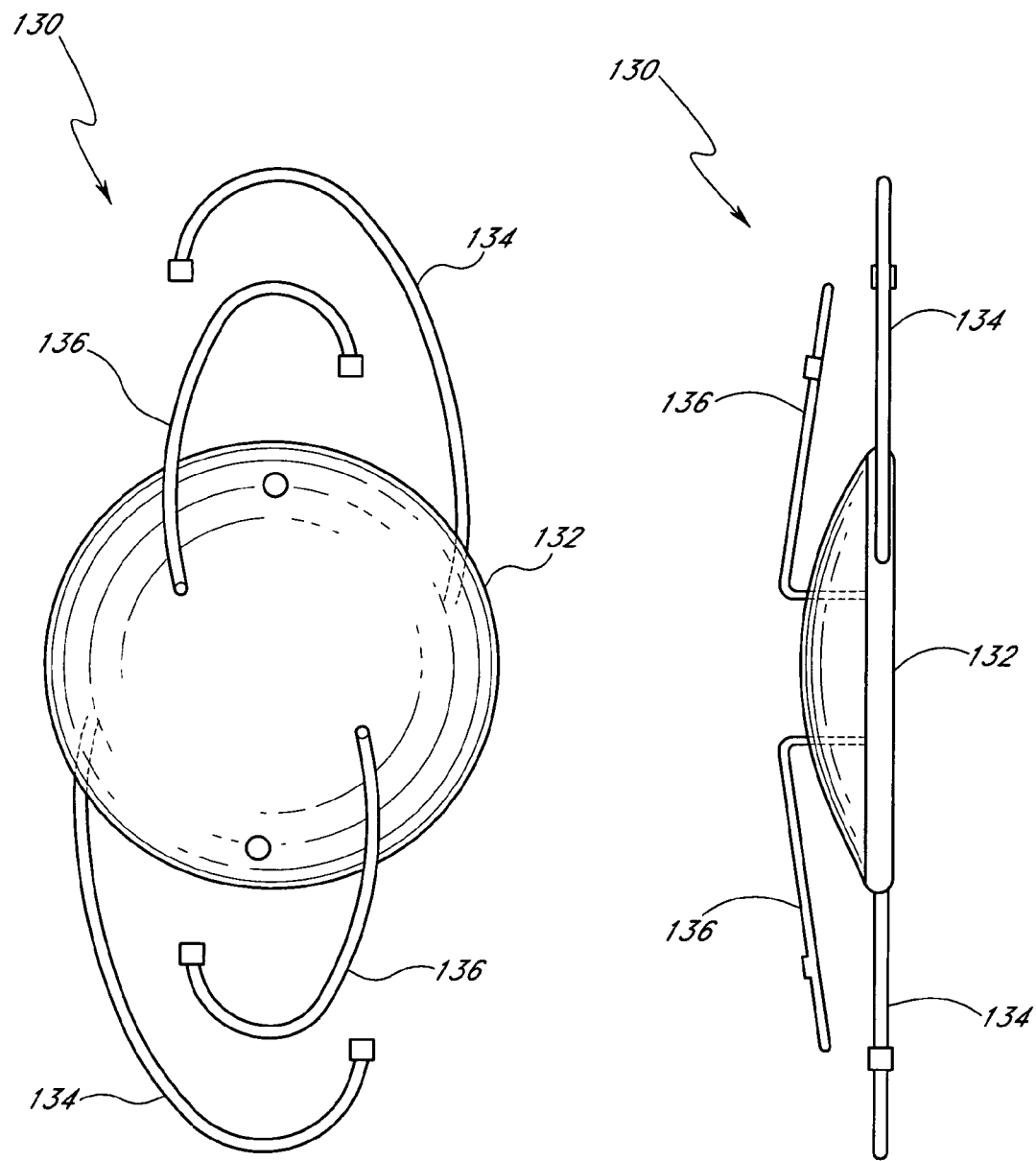
FIG. 14 is a top plan view of one embodiment of a posterior chamber intraocular lens.
FIG. 15 is a side view of the intraocular lens of FIG. 14.

FIGS. 14 and 15 show different views of one embodiment of a posterior chamber intraocular lens device 130. The lens 130 generally comprises an optic 132, support elements 134 and retaining elements 136.

Many other types of anterior chamber intraocular lens and posterior chamber intraocular lens as known in the art and/or commercially available may efficaciously be utilized in conjunction with the surgical procedures taught or suggested herein. These lenses may be implanted in the anterior chamber or posterior chamber of the eye, as needed or desired.

Figure 16:
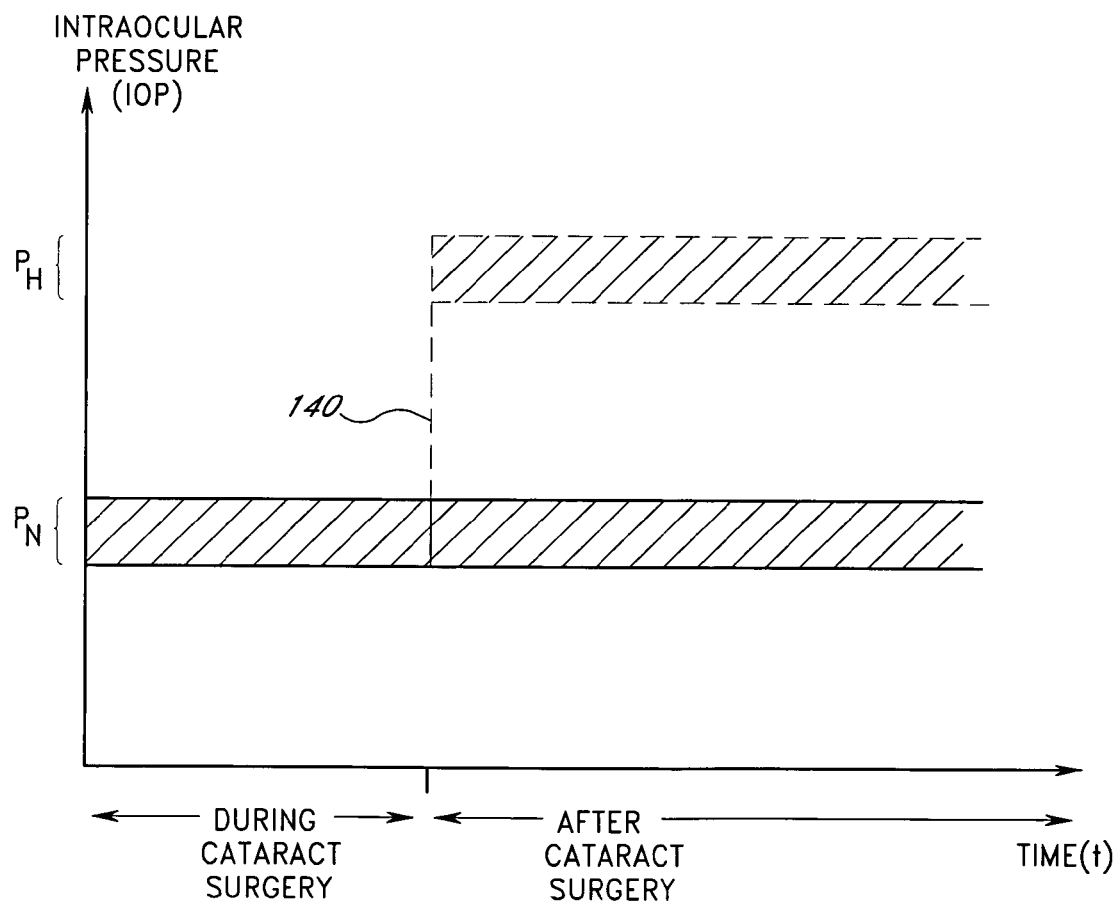
FIG. 16 is a simplified graphical representation of the intraocular pressure (IOP) during and after cataract surgery and illustrating the benefits of a preferred pressure control scheme in accordance with one embodiment of the invention.

During cataract surgery, typically the intraocular pressure is generally maintained by injecting viscoelastic fluid or physiological saline at a pre-specified pressure range ($P_N$ in FIG. 16). However, the pressure frequently undesirably spikes (as illustrated by line 140 in FIG. 16) to a high pressure or pressure range $P_H$ after closing the incision in the cornea (or limbus) because of "plugging" of the viscoelastic fluid. For a glaucoma patient, the combination of the pressure spike 140 and the inherent high intraocular pressure, possibly due to intolerance of glaucoma drugs post-operatively, complicates recovery of the cataract operations.

It is one aspect of the invention to provide a method of treating cataract of an eye while maintaining normal physiological intraocular pressure ($P_N$ in FIG. 16). The method generally comprising combination steps of establishing an opening through trabecular meshwork, removing the cataract, and inserting an intraocular lens, wherein the opening through trabecular meshwork comprises a trabecular stent having a lumen therein with optionally drug slow-releasing capability. The normal physiological intraocular pressure $P_N$ is preferably maintained between about 10 mm Hg (mercury) and 21 mm Hg, during and after the completion of the surgical procedure.

One modern technique for removing the central opaque part of the lens or cataract is a procedure called phacoemulsification. Typically, the pupil is dilated to facilitate access to the cataract. In the phacoemulsification procedure, a sophisticated ultrasonic titanium tipped instrument is introduced into the eye through an incision and passes through the anterior chamber. This titanium tip is ultrasonically vibrated against the lens in a manner which emulsifies the opaque central matrix of the lens.

Figure 17:
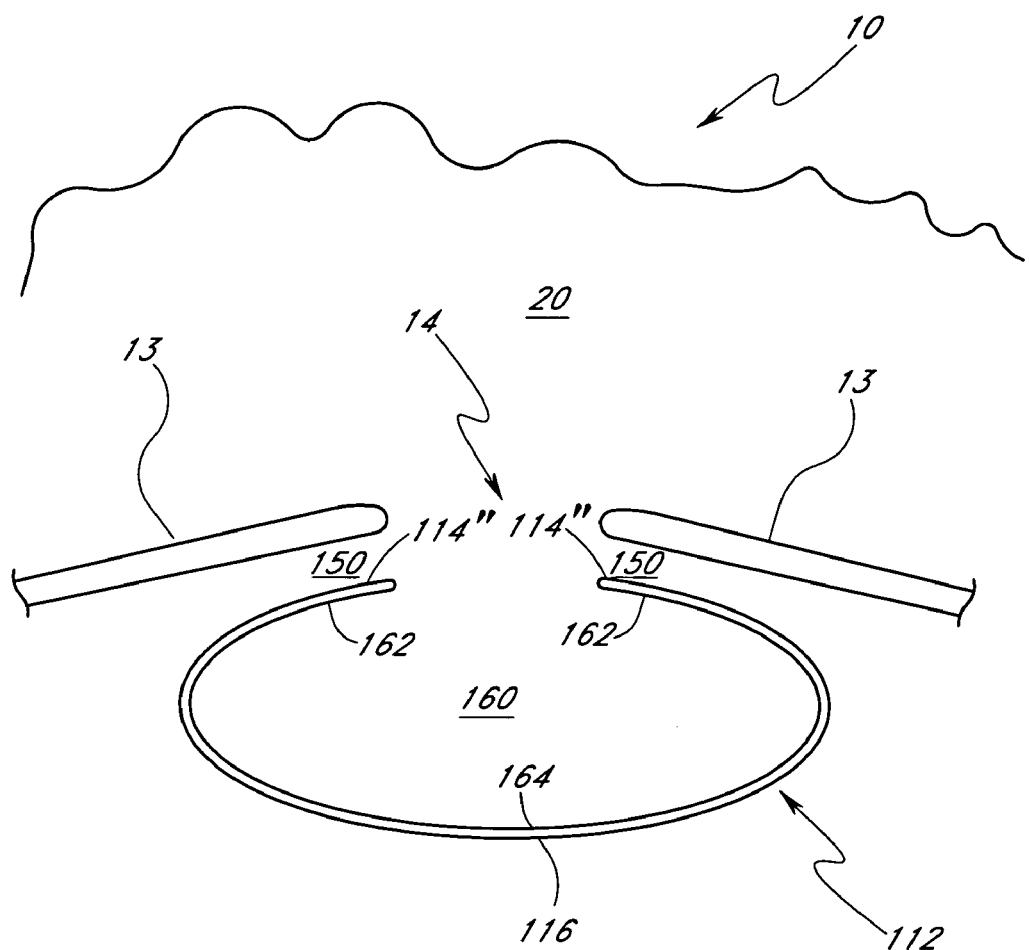
FIG. 17 is a simplified schematic view of a capsule of an eye after an extracapsular cataract extraction procedure.
Figure 17:
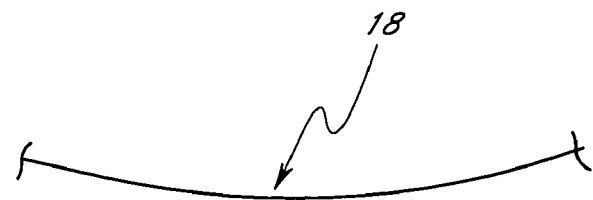

The emulsified matrix is then aspirated (using the same or different instrument) from the eye 10, and as best illustrated in FIG. 17, leaving the original posterior capsule or surface 116 of the lens intact with a small anterior capsular remnant or surface 114". When the capsule 112 or part of the capsule 112 is thus left inside the eye 10, the procedure is called extracapsular cataract extraction.

As illustrated by FIG. 17, extracapsular extraction allows the intraocular lens to be placed behind the iris 13 either in the space known as a ciliary sulcus 150, that is the space immediately behind the iris 13 and in front of the anterior capsule remnant 114" or in a space known as the capsular bag 160, that is between a posterior surface 162 of the anterior capsular flap 114" and an anterior surface 164 of the posterior capsule 116.

Overall Surgical Procedure

Figure 18:
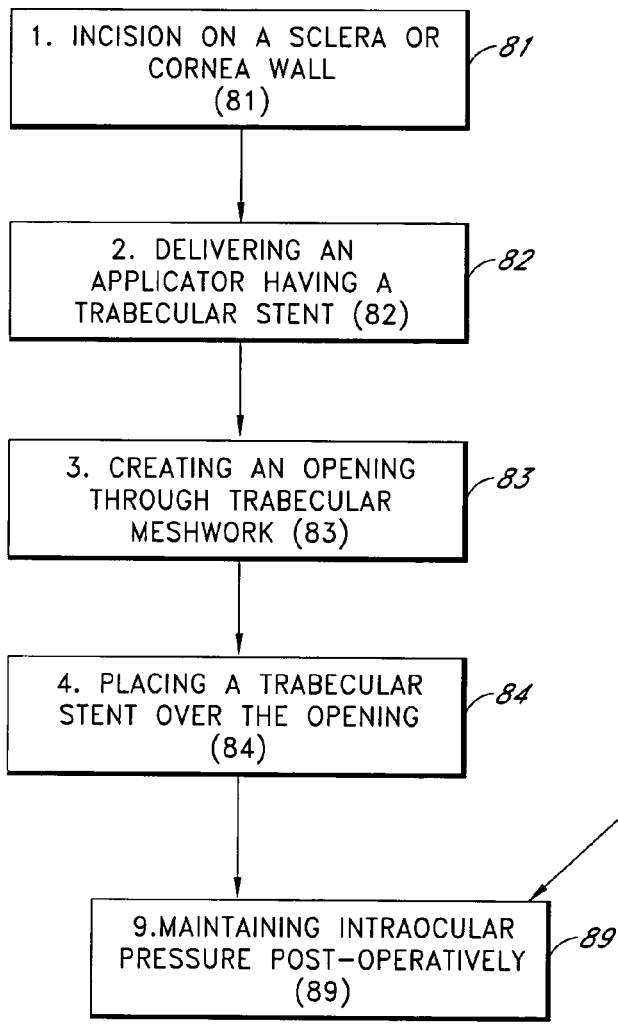
FIG. 18 is a simplified schematic block diagram illustrating steps of a combined procedure for cataract and glaucoma treatment having features and advantages in accordance with one embodiment of the invention.
Figure 18:
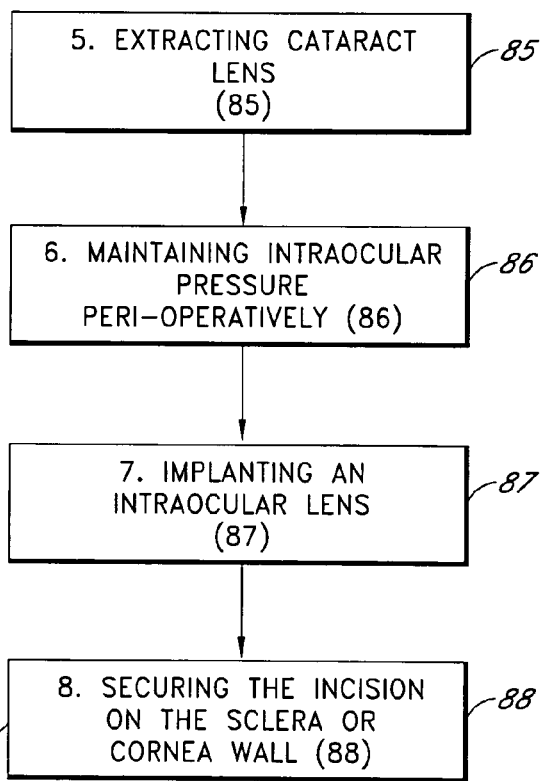

FIG. 18 shows a schematic diagram illustrating steps of a combined procedure for cataract and glaucoma treatment which advantageously controls or regulates the intraocular pressure (IOP) within a predetermined range. In some embodiments, the intraocular pressure is controlled during and after the surgical procedure. In other embodiments, the intraocular pressure is controlled only during a portion of the surgical procedure and after the surgical procedure. In yet other embodiments, the intraocular pressure is controlled only after the surgical procedure.

Preferably, an ab interno glaucoma procedure comprises one of the pre-cataract procedures. Optionally, an ab externo procedure may be utilized to lower IOP or treat glaucoma, as needed or desired.

In other embodiments, other pre-cataract procedures may include goniotomy, trabeculotomy, trabeculopuncture, goniophotoablation, laser trabecular ablation and goniocurretage. These embodiments and variations thereof can have numerous disadvantages and sub-optimal success rates because of undesirable tissue filling in.

As illustrated by FIG. 18, a stented ab interno glaucoma procedure (or lowering IOP procedure) may be conducted as a pre-cataract procedure in the cataract/glaucoma combination procedure. In other embodiments, the glaucoma procedure (or lowering IOP procedure) may be performed after the cataract surgery or procedure. In yet other embodiments, the glaucoma procedure (or lowering IOP procedure) may be combined with (before or after) other types of eye surgeries or procedures, for example, retinal surgery, vitrectomy, among others.

Referring in particular to FIG. 18, the accompanying ab interno glaucoma procedure comprises a step 81 of creating an incision on a sclera or cornea wall; a step 82 of delivering or providing an applicator having a trabecular stent 82; a step 83 of creating an opening through trabecular meshwork; and a step 84 of placing a trabecular stent over or through the opening while maintaining the intraocular pressure (IOP) peri-operatively. The opening in the trabecular meshwork may be made by a self-trephining stent, by the applicator itself or other cutting instrument as discussed above which is introduced through the incision in the cornea or sclera.

Still referring to FIG. 18, the main cataract procedure comprises a step 85 of extracting the diseased cataract lens; step 86 of maintaining the intraocular pressure peri-operatively within a specified range, step 87 of implanting an intraocular lens while maintaining IOP; and step 88 of securing the incision on the sclera or cornea wall while maintaining IOP. The step of extracting the cataract includes inserting an instrument (as described above) through the incision in the cornea or sclera. Advantageously, the accompanying glaucoma procedure provides the eye with a balanced intraocular pressure post-operatively in step 89 without the need of a IOP-lowering drug that may complicate the surgical success of the intended cataract procedure.

Advantageously, a single incision in the cornea or sclera may be used to perform both (or multiple) surgical procedures. Moreover, and desirably, the glaucoma and cataract may be treated in a single visit operation that may be performed as an outpatient procedure with rapid visual recovery and greatly decreased morbidity.

It should be noted that even patients without high IOP (or glaucoma) may develop temporary glaucoma or high IOP due to edema or swelling caused by the cataract procedure or other eye surgery. In such cases, the stent can lower the IOP or a temporary opening may be created in the trabecular meshwork which fills in over time but temporarily allows lowering of the IOP for a certain time period.

From the foregoing description, it will be appreciated that a novel approach for the surgical treatment of glaucoma and cataract in one single operation (or one visit) has been disclosed for releasing excessive or elevated intraocular pressure and correcting or treating cataract. While the components, techniques and aspects of the invention have been described with a certain degree of particularity, it is manifest that many changes may be made in the specific designs, constructions and methodology herein above described without departing from the spirit and scope of this disclosure.

Various modifications and applications of the invention may occur to those who are skilled in the art, without departing from the true spirit or scope of the invention. It should be understood that the invention is not limited to the embodiments set forth herein for purposes of exemplification, but is to be defined only by a fair reading of the appended claims, including the full range of equivalency to which each element thereof is entitled.

What is claimed is:

1. A method, of performing a combined surgery on an eye, comprising:
providing an opening into an anterior chamber of the eye;
extracting a cataract from the eye through the opening;
providing an ocular implant having an inflow portion in fluid communication with an outflow portion of the ocular implant;
transporting the ocular implant on a guide member through the anterior chamber of the eye to a uveal scleral outflow pathway of the eye;
moving the ocular implant relative to the guide member to position the ocular implant such that the inflow portion of the ocular implant is positioned in the anterior chamber and the outflow portion of the ocular implant is positioned in the uveal scleral outflow pathway; and
permitting aqueous humor to flow from the anterior chamber of the eye through the inflow portion of the ocular implant to the outflow portion of the ocular implant and into the uveal scleral outflow pathway of the eye.

2. The method of claim 1, wherein extracting the cataract is performed prior to positioning the ocular implant.

3. The method of claim 1, wherein positioning the ocular implant is performed prior to extracting the cataract.

4. The method of claim 1, wherein extracting the cataract comprises phacoemulsification of a lens of the eye.

5. The method of claim 1, wherein the combined surgery comprises lowering intraocular pressure of the eye.

6. The method of claim 5, wherein the lowering of intraocular pressure is a treatment for glaucoma.

7. The method of claim 1, wherein said ocular implant comprises a tube.

8. The method of claim 1, wherein said ocular implant comprises a cutting tip for making an incision in eye tissue.

9. The method of claim 1, wherein extracting the cataract comprises using an ultrasonic instrument.

10. The method of claim 1, wherein transporting the ocular implant comprises using an applicator.

11. The method of claim 10, wherein said applicator comprises an actuator to release said ocular implant from said applicator.

12. A method, of performing a combined surgery on an eye, comprising:
providing an opening into an anterior chamber of the eye;
extracting a cataract from the eye through the opening;
providing an ocular implant having an inflow portion in fluid communication with an outflow portion of the ocular implant;
transporting the ocular implant on a guide member through the anterior chamber of the eye to an aqueous collector channel of the eye;
moving the ocular implant relative to the guide member to position the ocular implant such that the inflow portion of the ocular implant is positioned in the anterior chamber and the outflow portion of the ocular implant is positioned in the aqueous collector channel; and permitting aqueous humor to flow from the anterior chamber of the eye through the inflow portion of the ocular implant to the outflow portion of the ocular implant and into the aqueous collector channel of the eye.

13. The method of claim 12, wherein extracting the cataract is performed prior to positioning the ocular implant.

14. The method of claim 12, wherein positioning the ocular implant is performed prior to extracting the cataract.

15. The method of claim 12, wherein extracting the cataract comprises phacoemulsification of a lens of the eye.

16. The method of claim 12, wherein the combined surgery comprises lowering intraocular pressure of the eye.

17. The method of claim 16, wherein the lowering of intraocular pressure is a treatment for glaucoma.

18. The method of claim 12, wherein said method further comprises making an incision in trabecular meshwork of the eye for receiving said ocular implant.

19. The method of claim 12, wherein said ocular implant comprises a tube.

20. The method of claim 12, wherein said ocular implant comprises a cutting tip for making an incision in eye tissue.

21. The method of claim 12, wherein extracting the cataract comprises using an ultrasonic instrument.

22. The method of claim 12, wherein transporting the ocular implant comprises using an applicator.

23. The method of claim 22, wherein said applicator comprises an actuator to release said ocular implant from said applicator.

* * * * *

UNITED STATES PATENT AND TRADEMARK OFFICE
CERTIFICATE OF CORRECTION

| | | |
|---|---|---|
| PATENT NO. | : 7,951,155 B2 | Page 1 of 1 |
| APPLICATION NO. | : 11/653815 | |
| DATED | : May 31, 2011 | |
| INVENTOR(S) | : Gregory T. Smedley et al. | |

It is certified that error appears in the above-identified patent and that said Letters Patent is hereby corrected as shown below:

On Page 4, Column 2 (Item 56), Line 30, Under other Publications, please change "Opbhthalmol" to --Ophthalmol--.

In Column 1, Line 14, please change "on" to --one--.

In Column 2, Line 38, please change "juxtacanilicular" to --juxtacanalicular--.

In Column 2, Line 40, please change "juxtacanilicular" to --juxtacanalicular--.

In Column 6, Line 50, please change "mergers" to --merges--.

In Column 6, Line 53, please change "layer" to --vascular layer--.

In Column 7, Line 53, please change "wafarin," to --warfarin,--.

In Column 7, Line 54, please change "forskplin," to --forskolin,--.

In Column 8, Line 34, please change "31 A" to --31A--.

In Column 9, Line 52, please change "pyrolidone," to --pyrrolidone,--.

In Column 11, Line 11, please change "H D" to --HD--.

In Column 11, Lines 29-30, please change "juxtacanilicular" to --juxtacanalicular--.

In Column 11, Line 67, please change "torasernide" to --torsemide--.

In Column 12, Line 4, please change "quinoxoalines" to --quinoxalines--.

In Column 13, Line 14, please change "non-comeotoxic" to --non-corneotoxic--.

In Column 16, Line 3, please change "microcurrette." to --microcurette.--.

In Column 16, Line 5, please change "fiberoptic" to --fiber optic--.

In Column 16, Line 50, please change "BIFURACATABLE" to --BIFURCATABLE--.

In Column 17, Line 17, please change "surface" to --surfaces--.

In Column 17, Line 24, please change "opacacified" to --opacified--.

In Column 17, Lines 35-36, please change "(polyhyroxyethylmethymethacrylate)," to --(polyhydroxyethylmethacrylate),--.

Signed and Sealed this
Twenty-ninth Day of May, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,951,155 B2 | |
| APPLICATION NO. | : 10/893764 | |
| DATED | : May 31, 2011 | |
| INVENTOR(S) | : Smedley et al. | |

It is certified that error appears in the above-identified patent and that said Letters Patent is hereby corrected as shown below:

Title Page, Item (75), should read:

-- Inventors:
(75) Inventors: Gregory T. Smedley, Irvine, CA (US); David Haffner, Mission Viejo, CA (US); Barbara Niksch, Laguna Niguel, CA (US); Hosheng Tu, Newport Coast, CA (US); Thomas W. Burns, Laguna Niguel, CA (US) --.

Signed and Sealed this
Seventeenth Day of March, 2015

Michelle K. Lee
*Director of the United States Patent and Trademark Office*